United States Patent
Niwa et al.

(12)

(10) Patent No.: US 6,508,106 B1
(45) Date of Patent: Jan. 21, 2003

(54) METHOD AND APPARATUS FOR MEASURING VISCOSITY OF GREEN COMPACT, AND COMPUTER READABLE RECORDING MEDIUM FOR STORING METHOD FOR MEASURING VISCOSITY OF GREEN COMPACT

(75) Inventors: Yoshihito Niwa, Kyoto (JP); Hiroshi Takagi, Otsu (JP)

(73) Assignee: Murata Manufacturing Co., LTD, Kyoto (JP)

( * ) Notice: Subject to any disclaimer, the term of this patent is extended or adjusted under 35 U.S.C. 154(b) by 60 days.

(21) Appl. No.: 09/679,208

(22) Filed: Oct. 4, 2000

(30) Foreign Application Priority Data

Oct. 4, 1999 (JP) ............................................. 11-283210
Nov. 2, 1999 (JP) ............................................. 11-312507

(51) Int. Cl.$^7$ ............................................... G01N 11/00
(52) U.S. Cl. ..................................... 73/54.01; 73/54.39
(58) Field of Search ............................... 73/54.01, 54.39

(56) References Cited

PUBLICATIONS

Yuanzheng, Y. et al. "A New Description and Interpretation of the Flow Behaviour of Glass Forming Melts", Journal of Non–Crystalline Solids, vol. 180, 1994, pp. 66–79.*

British Journal of Applied Physics, vol. 11, "Theory of the parallel plate viscometer", A.N. Gent, Feb. 1960.

* cited by examiner

*Primary Examiner*—Daniel S. Larkin
(74) *Attorney, Agent, or Firm*—Keating & Bennett, LLP

(57) ABSTRACT

A method for measuring the viscosity of a green compact includes the steps of finding a corrected value V' of the sample volume of the green compact, where the corrected value V' of the sample volume is a volume occupied by the inorganic powder in the green compact; finding a corrected value (dh/dt)' of the sample deformation rate of the green compact, where the corrected value (dh/dt)' of the sample deformation rate is the difference between the apparent sample deformation rate and the sample deformation rate due to sintering shrinkage; separating a temperature range X in which sintering shrinkage dominates and a temperature range Y in which plastic deformation dominates with respect to the displacement of the green compact; substituting the corrected value V' of the sample volume for the sample volume V and substituting the corrected value (dh/dt)' of the sample deformation rate for the sample deformation rate dh/dt in the Gent equation with respect to the temperature range X; and substituting the corrected value V' of the sample volume for the sample volume V in the Gent equation with respect to the temperature range Y.

25 Claims, 30 Drawing Sheets

DIFFERENCE IN VISCOUS BEHAVIOR BETWEEN
BULK SAMPLE AND GREEN COMPACT

GREEN COMPACT

WEIGHT OF INORGANIC POWDER $m_1$ (g)
ABSOLUTE SPECIFIC GRAVITY OF
INORGANIC POWDER $n_1$ (g/cm$^3$)
WEIGHT OF GREEN COMPACT SAMPLE m (g)
AMOUNT OF INORGANIC POWDER $w_1$ (g)
AMOUNT OF VEHICLE $w_2$ (g)

$V' = m_1/n_1$
$m_1 = m_x \{w_1/(w_1 + w_2)\}$

CORRECTED VALUE OF SAMPLE VOLUME

FIG. 2

GLASS (BULK)

DIFFERENCE IN VISCOUS BEHAVIOR OF GLASS BY
CALCINING TEMPERATURE OF GREEN COMPACT

SAMPLE 1 (CALCINING TEMPERATURE: SOFTENING POINT)

DIFFERENCE IN VISCOUS BEHAVIOR OF GLASS BY
CALCINING TEMPERATURE OF GREEN COMPACT

SAMPLE 1 (CALCINING TEMPERATURE: SOFTENING POINT MINUS 10°C)

DIFFERENCE IN VISCOUS BEHAVIOR OF GLASS BY
CALCINING TEMPERATURE OF GREEN COMPACT

SAMPLE 1 (CALCINING TEMPERATURE: SOFTENING POINT MINUS 20°C)

DIFFERENCE IN VISCOUS BEHAVIOR OF GLASS BY
CALCINING TEMPERATURE OF GREEN COMPACT

SAMPLE 1 (CALCINING TEMPERATURE: SOFTENING POINT MINUS 30°C)

DIFFERENCE IN VISCOUS BEHAVIOR OF GLASS BY
CALCINING TEMPERATURE OF GREEN COMPACT

SAMPLE 1 (CALCINING TEMPERATURE: SOFTENING POINT MINUS 50°C)

DIFFERENCE IN VISCOUS BEHAVIOR OF GLASS BY
CALCINING TEMPERATURE OF GREEN COMPACT

SAMPLE 2 (CALCINING TEMPERATURE: SOFTENING POINT)

DIFFERENCE IN VISCOUS BEHAVIOR OF GLASS BY
CALCINING TEMPERATURE OF GREEN COMPACT

SAMPLE 2 (CALCINING TEMPERATURE: SOFTENING POINT MINUS 10°C)

DIFFERENCE IN VISCOUS BEHAVIOR OF GLASS BY
CALCINING TEMPERATURE OF GREEN COMPACT

SAMPLE 2 (CALCINING TEMPERATURE: SOFTENING POINT MINUS 20°C)

DIFFERENCE IN VISCOUS BEHAVIOR OF GLASS BY
CALCINING TEMPERATURE OF GREEN COMPACT

SAMPLE 2 (CALCINING TEMPERATURE: SOFTENING POINT MINUS 30°C)

DIFFERENCE IN VISCOUS BEHAVIOR OF GLASS BY CALCINING TEMPERATURE OF GREEN COMPACT

SAMPLE 2 (CALCINING TEMPERATURE: SOFTENING POINT MINUS 50°C)

DIFFERENCE IN VISCOUS BEHAVIOR OF GLASS BY CALCINING TEMPERATURE OF GREEN COMPACT

SAMPLE 3 (CALCINING TEMPERATURE: SOFTENING POINT )

DIFFERENCE IN VISCOUS BEHAVIOR OF GLASS BY
CALCINING TEMPERATURE OF GREEN COMPACT

SAMPLE 3 (CALCINING TEMPERATURE: SOFTENING POINT MINUS 10°C)

DIFFERENCE IN VISCOUS BEHAVIOR OF GLASS BY
CALCINING TEMPERATURE OF GREEN COMPACT

SAMPLE 3 (CALCINING TEMPERATURE: SOFTENING POINT MINUS 20°C)

DIFFERENCE IN VISCOUS BEHAVIOR OF GLASS BY
CALCINING TEMPERATURE OF GREEN COMPACT

SAMPLE 3 (CALCINING TEMPERATURE: SOFTENING POINT MINUS 30°C)

DIFFERENCE IN VISCOUS BEHAVIOR OF GLASS BY
CALCINING TEMPERATURE OF GREEN COMPACT

SAMPLE 3 (CALCINING TEMPERATURE: SOFTENING POINT MINUS 50°C)

PARALLEL PLATE VISCOMETER

METHOD AND APPARATUS FOR MEASURING VISCOSITY OF GREEN COMPACT, AND COMPUTER READABLE RECORDING MEDIUM FOR STORING METHOD FOR MEASURING VISCOSITY OF GREEN COMPACT

BACKGROUND OF THE INVENTION

1. Field of the Invention

The present invention relates to a method for measuring the viscosity of a green compact sample formed by compaction molding of crystallized glass powder and the like, an apparatus for measuring the viscosity of a green compact sample, and a computer readable recording medium for storing the method for measuring the viscosity of the green compact sample.

Furthermore, the present invention relates to a method for measuring the viscosity of a green compact sample formed by compaction molding of amorphous glass powder and the like.

2. Description of the Related Art

Recently, in the electronics industry, various researches and developments have been made on ceramic multilayered substrates and thick-film materials which can meet higher densities for mounting components and circuit conductors, higher signal frequencies, etc. In particular, ceramic multilayered substrates which are formed by firing composite materials containing amorphous glass powder and crystallized glass can satisfactorily meet the higher density and higher frequency requirements because they have small relative dielectric constants and they can be fired simultaneously with Ag conductive materials having small resistivity.

In such ceramic multilayered substrates and thick-film materials, physical properties of inorganic oxide powder, such as amorphous glass powder and crystallized glass powder, strongly affect the substrate characteristics and thick-film characteristics. In particular, the viscosity characteristics thereof greatly affect the sintering process of the inorganic oxide powder, the diffusion behavior of Ag conductive materials, and so on, thus being significantly important parameters in material design and process design.

In general, in order to measure the viscosity of such glass powders, an extended fiber viscometer is used in the high viscosity region of approximately $10^{10}$ Pa·s or more, and a rotary viscometer (draw sphere viscometer) is used in the low viscosity region of approximately $10^4$ Pa·s or less. The viscosity is measured by a parallel plate viscometer in the intermediate viscosity region of $10^4$ to $10^9$ Pa·s, which is particularly important in the sintering process of such glass powders.

A method for measuring viscosity $\eta$ by a parallel plate viscometer will be described below.

First, as shown in FIG. 31, a test piece (sample) 1 in which the height H and the volume V have been accurately measured is placed on a quartz plate 2a which is fixed on a support 3. The test piece 1 is then sandwiched between the quartz plate 2a and a quartz plate 2b which is fixed to a quartz rod 4, and while a certain load M is applied to the quartz rod 4 and an apparatus 6 is heated by a heater 5, the displacement (height H) of the test piece 1 is detected by a differential transducer (not shown in the drawing) interlocking the quartz rod 4. By extracting the displacement over time, a sample deformation rate dh/dt of the test piece 1 is calculated.

Next, the sample volume V, the load M, and the sample deformation rate dh/dt are substituted into the Gent equation below to calculate the viscosity $\eta$ of the test piece 1 (refer to A. N. Gent, British Journal of Applied Physics, Vol. 11, Feb. 1960).

$$\eta = 2\pi M G H^5 / \{3V(dh/dt)(2\pi H^3 + V)\}$$

where M is the load, H is the height of the sample, G is the gravitational acceleration, V is the sample volume, and dh/dt is the sample deformation rate.

By performing the above for each temperature, and a variation of viscosity $\eta$ with temperature, that is a viscosity-temperature curve is derived.

However, in the measurement of viscosity by the parallel plate viscometer described above, a bulk sample must be used as the test piece 1. That is, the Gent equation is only applicable in a case where the test piece 1 can be assumed to be an incompressible fluid. For example, when the viscosity of glass powder is measured, a bulk sample in which the glass powder is melted, quenched, and formed into a bulk material must be used.

That is, in the method described above, although the viscosity of glass which is formed into a bulk can be measured, it is difficult to measure the viscosity of glass in the powder state, in particular, the viscosity of crystallized glass powder. This is because of the fact that in the crystallized glass powder which tends to be crystallized, crystals may be precipitated during the formation of a bulk sample. Even if a bulk sample is formed, since the crystallization behavior is essentially different between the bulk sample and the powder sample, the viscous behavior differs between the bulk sample and the powder sample even with respect to the same type of glass powder.

However, as described above, in most of the ceramic multilayered substrates and thick-film materials, crystallized glass, amorphous glass, and the like are used as powder samples. That is, in view of material design and process design, evaluation of viscosity characteristics as powder samples must be performed with respect to crystallized glass, amorphous glass, and the like.

SUMMARY OF THE INVENTION

Accordingly, it is an object of the present invention to provide a method for measuring the viscosity of a green compact sample formed by compaction molding of inorganic powder with high accuracy. It is another object of the present invention to provide an apparatus for efficiently measuring the viscosity of a green compact sample. It is another object of the present invention to provide a computer readable recording medium for storing the method for measuring the viscosity of the green compact sample.

In one aspect of the present invention, in a method for measuring the viscosity of a green compact sample, the viscosity $\eta$ of a green compact sample formed by compaction molding of inorganic powder is measured in accordance with the Gent equation:

$$\eta = 2\pi M G H^5 / \{3V(dh/dt)(2\pi H^3 + V)\}$$

where M is the load, H is the height of the sample, G is the gravitational acceleration, V is the sample volume, and dh/dt is the sample deformation rate.

The method includes the steps of:

(A) finding a corrected value V' of the sample volume of the green compact sample, where the corrected value V' of the sample volume is a volume occupied by the inorganic powder in the green compact sample;

(B) finding a corrected value (dh/dt)' of the sample deformation rate of the green compact sample, where the corrected value (dh/dt)' of the sample deformation rate is the difference between the apparent sample deformation rate and the sample deformation rate due to sintering shrinkage;

(C) separating a temperature range X in which sintering shrinkage dominates and a temperature range Y in which plastic deformation dominates with respect to the displacement of the green compact sample;

(D) substituting the corrected value V' of the sample volume for the sample volume V and substituting the corrected value (dh/dt)' of the sample deformation rate for the sample deformation rate dh/dt in the Gent equation with respect to the temperature range X in which sintering shrinkage dominates; and (E) substituting the corrected value V' of the sample volume for the sample volume V in the Gent equation with respect to the temperature range Y in which plastic deformation dominates.

In the method for measuring the viscosity of the green compact sample in the present invention, with respect to the measurement of viscosity which has been conventionally applied only to an incompressible fluid, such as a bulk sample, by executing (A) a step of extracting the corrected value V' of the sample volume by correcting the sample volume, (B) a step of extracting the corrected value (dh/dt)' of the sample deformation rate by correcting the sample deformation rate, and (C) a step of separating the temperature range X in which sintering shrinkage dominates and the temperature range Y in which plastic deformation dominates with respect to the displacement of the green compact sample, and further by executing, in the Gent equation, (D) correction of the sample volume and correction of the sample deformation rate in the temperature range X in which sintering shrinkage dominates, and (E) correction of the sample volume in the temperature range Y in which plastic deformation dominates, the viscosity of the green compact sample which exhibits viscous behavior which is very close to that in the powder sate can be measured with high accuracy.

In another aspect of the present invention, in an apparatus for measuring the viscosity of a green compact sample, the viscosity $\eta$ of a green compact sample formed by compaction molding of inorganic powder is measured in accordance with the Gent equation:

$$\eta = 2\pi MGH^5 / \{3V(dh/dt)(2\pi H^3 + V)\}$$

where M is the load, H is the height of a sample, G is the gravitational acceleration, V is the sample volume, and dh/dt is the sample deformation rate.

The apparatus includes:

(a) a sample shape measuring unit for measuring actual shape values of the green compact sample;

(b) a sample deformation rate measuring unit for measuring the apparent sample deformation rate of the green compact sample;

(c) an arithmetic processing unit for calculating the volume occupied by the inorganic powder in the green compact sample based on the actual shape values of the green compact sample and for outputting a sample volume corrected value V';

(d) an arithmetic processing unit for calculating the difference between the apparent sample deformation rate and the sample deformation rate due to sintering shrinkage of the green compact sample and for outputting a sample deformation rate corrected value (dh/dt)' of the green compact sample;

(e) an arithmetic processing unit for plotting a boundary temperature between a temperature range X in which sintering shrinkage dominates and a temperature range Y in which plastic deformation dominates with respect to the displacement of the green compact sample;

(f) an arithmetic processing unit for outputting the viscosity $\eta$ in the temperature range X by substituting the sample volume corrected value V' for the sample volume V and by substituting the sample deformation rate corrected value (dh/dt)' for the sample deformation rate dh/dt in the Gent equation with respect to the temperature range X in which sintering shrinkage dominates;

(g) an arithmetic processing unit for outputting the viscosity $\eta$ in the temperature range Y by substituting the sample volume corrected value V' for the sample volume V in the Gent equation with respect to the temperature range Y in which plastic deformation dominates; and (h) a display for displaying the viscosity $\eta$ in the temperature range X and the viscosity $\eta$ in the temperature range Y.

In the apparatus for measuring the viscosity of the green compact sample in the present invention, since the apparatus includes (a) the sample shape measuring unit and (b) the sample deformation rate measuring unit, the individual arithmetic processing units (c) for the extraction of the sample volume corrected value V' by correcting the sample shape, (d) for the extraction of the sample deformation rate corrected value (dh/dt)' by correcting the sample deformation rate, (e) for separating the temperature range X in which sintering shrinkage dominates and the temperature range Y in which plastic deformation dominates, (f) for correcting the sample volume and the sample deformation rate in the Gent equation with respect to the temperature range X in which sintering shrinkage dominates, and (g) for correcting the sample volume in the Gent equation with respect to the temperature range Y in which plastic deformation dominates, and (h) the display for displaying the results of the arithmetic processes, i.e., the viscosity $\eta$ of the green compact sample in each temperature range, it is possible to efficiently measure the viscosity of the green compact sample which exhibits viscous behavior very close to that in the powder state by using the Gent equation which has been conventionally applicable only to an incompressible fluid, such as a bulk sample.

In another aspect of the present invention, a computer readable recording medium for storing the method for measuring the viscosity of a green compact sample is provided with a program for executing the method for measuring the viscosity of the green compact sample in the present invention.

Since the computer readable recording medium for storing the method for measuring the viscosity of the green compact sample in the present invention is provided with the program for executing the method for measuring the viscosity of the green compact sample in the present invention, it is possible to store the method for measuring viscosity of the green compact sample in the present invention and to easily transfer the technology thereof, facilitating the use thereof by many people.

In another aspect of the present invention, in a method for measuring the viscosity of a green compact sample in which the viscosity $\eta$ of a green compact sample formed by compaction molding of inorganic powder is measured in accordance with the Gent equation:

$$\eta = 290\, MGH^5/\{3V(dh/dt)(2\pi H^3 + V)\}$$

where M is the load, H is the height of the sample, G is the gravitational acceleration, V is the sample volume, and dh/dt is the sample deformation rate, the measurement is performed using the green compact sample which is preliminarily calcined.

In the method for measuring the viscosity of the green compact sample, by preliminarily calcining the green compact sample, particles of the inorganic powder are sufficiently brought into close contact with each other (necked), and the viscous behavior thereof becomes very close to that of an incompressible fluid, and thus it is possible to measure the viscosity with high accuracy with respect to the green compact sample which exhibits viscous behavior that is very close to that of the inorganic powder in the powder state.

BRIEF DESCRIPTION OF THE DRAWINGS

FIG. 2 is a flowchart which shows a step of extracting a corrected value of a sample volume in a method for measuring the viscosity of a green compact sample in the present invention;

DESCRIPTION OF THE PREFERRED EMBODIMENTS

First Embodiment

A method for measuring the viscosity of a green compact sample in the present invention will be described in detail below.

In general, in a method for measuring viscosity using a parallel plate viscometer, the viscosity η of a sample with a volume V is calculated in accordance with the Gent equation:

$$\eta = 2\pi MGH^5 / \{3V(dh/dt)(2\pi H^3 + V)\}$$

where M is the load, H is the height of the sample, G is the gravitational acceleration, V is the sample volume, and dh/dt is the sample deformation rate.

Figure 1:
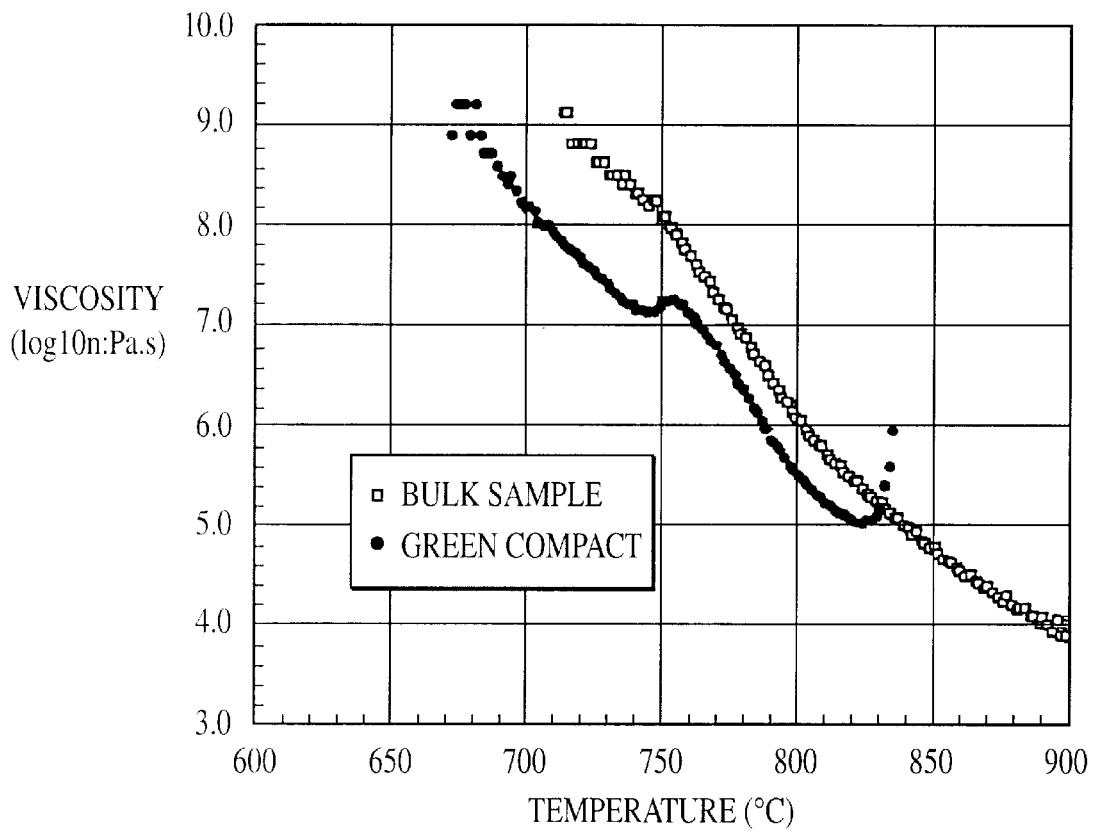
FIG. 1 is a graph illustrating viscosity-temperature curves which show a difference in viscous behavior between a bulk sample and a green compact sample.

FIG. 1 is a graph which shows viscosity-temperature curves of a bulk sample and a green compact sample with respect to $SiO_2$—$B_2O_3$—$Al_2O_3$—CaO-based crystallized glass powder, which will be described below, when the Gent equation is applied. The bulk sample is formed by melting the crystallized glass powder at 1,650° C., maintaining it at 650° C. for 30 minutes in a lehr, and slow-cooling at 2° C./minute. The green compact sample is formed by compaction molding the crystallized glass powder together with an organic vehicle.

As is obvious from FIG. 1, the viscosity-temperature curve for the bulk sample and the viscosity-temperature curve for the green compact sample do not correspond to each other only by simply applying the sample deformation rate by the parallel plate viscometer and the sample volume to the Gent equation. That is, despite the viscosity measurement of crystallized glass powder of the same type, it appears that the viscous behavior greatly differs between the bulk sample and the green compact sample.

First, an increase in viscosity is observed at approximately 830° C. in the green compact sample, which does not apply to the bulk sample. The increase in viscosity is mainly caused by a difference in ease of crystallization between the green compact sample and the bulk sample. That is, as is clear from the results of thermal analysis (DSC analysis) shown in Table 1 below, the green compact sample has a lower crystallization temperature ($T_c$) and a lower crystallization peak temperature ($T_{cp}$) than those of the bulk sample, both being approximately 150° C. to 160° C. lower.

TABLE 1

|  | $T_c$ (° C.) | $T_{cp}$ (° C.) |
|---|---|---|
| Green Compact Sample | 818 | 843 |
| Bulk Sample | 966 | 1,009 |

This is because of the fact that since the green compact sample has a larger specific surface area than that of the bulk sample, crystallization (nucleation of a crystal phase, or nuclear growth) is easily accelerated from the surface of the crystallized glass powder, and thus the crystallization temperature shifts to a lower temperature.

Next, as shown in FIG. 1, the viscosity-temperature curve for the green compact sample substantially falls far below the viscosity-temperature curve for the bulk sample, and although the viscosity-temperature curve for the green compact sample comes close to the viscosity-temperature curve for the bulk sample in the viscosity range that is lower than approximately $10^7 Pa \cdot s$, it still lies on the lower viscosity side.

As described above, the Gent equation is only applicable in a case where a test piece can be assumed to be an incompressible fluid. In contrast, in the green compact sample, which is solidified by compaction molding the inorganic powder and the vehicle, a change in volume occurs due to sintering shrinkage as firing advances, and thus the green compact sample cannot be considered as an incompressible fluid.

That is, it is not possible to consider the result obtained by simply applying measurements of the green compact sample to the Gent equation in a manner similar to that of the bulk sample as the viscosity of the green compact sample. Parameters in the Gent equation must be corrected in order to make the Gent equation also applicable to the green compact sample.

For that purpose, first, in order to correct a substantial difference in volume between the bulk sample and the green compact sample, a volume obtained by multiplying an apparent volume of the green compact sample by a filling factor of the crystallized glass powder in the green compact sample is considered as a corrected value V' of the sample volume, and the corrected value V' is substituted into the Gent equation. Additionally, the filling factor of the crystallized glass powder can be easily calculated based on the absolute specific gravity of the crystallized glass powder, the compositional ratio of the inorganic powder, and the weight of the green compact sample.

For example, as shown in a flowchart in FIG. 2, by measuring the weight $m_1$ of inorganic powder of crystallized glass or the like, the absolute specific gravity $n_1$, the weight m of a green compact sample, the amount $w_1$ of inorganic powder, the amount w2 of a vehicle, a corrected value V' of the sample volume can be calculated in accordance with the equations below.

$$V' = m_1/n_1$$

$$m_1 = m \times \{w_1/(w_1+w_2)\}$$

Secondly, in a temperature range in which sintering shrinkage dominates with respect to the displacement of the green compact sample, a sample deformation rate due to sintering shrinkage must be taken into consideration. That is, as shown in FIG. 3, since the apparent sample deformation rate of a green compact sample includes a sample deformation rate due to plastic deformation and a sample deformation rate due to sintering shrinkage, a sample deformation rate in which the above two sample deformation rates are offset, i.e., a sample deformation rate corrected value (dh/dt)', must be applied to the Gent equation.

Figure 3:
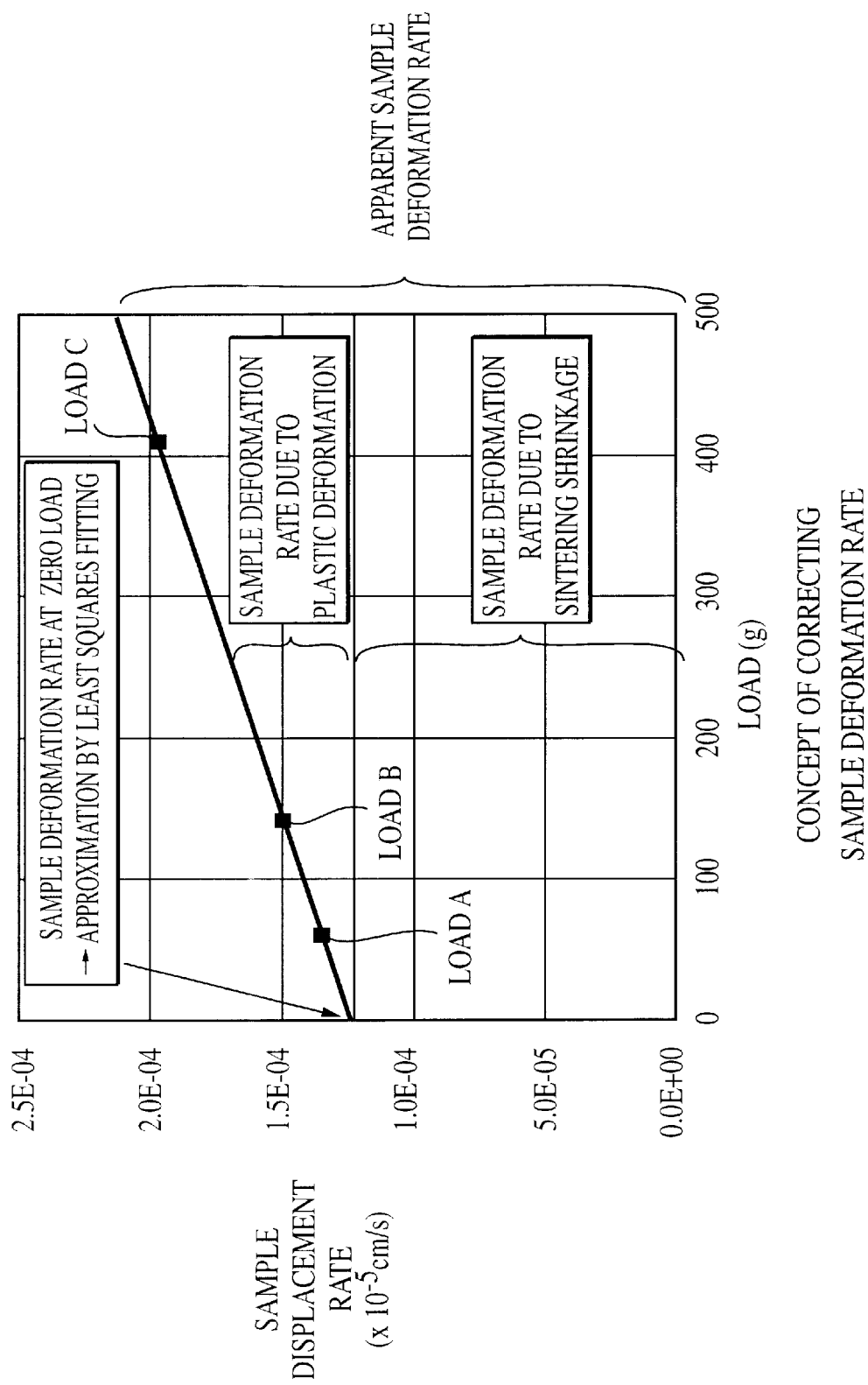
FIG. 3 is a graph which schematically shows the correction of a sample deformation rate in a method for measuring the viscosity of a green compact sample in the present invention.

As shown in FIG. 3, in a temperature range X in which sintering shrinkage dominates, a sample deformation rate $(dh/dt)_0$ at zero load can be considered as a sample deformation rate due to sintering shrinkage. Therefore, in order to derive the sample deformation rate with respect to the temperature range X, the sample deformation rate $(dh/dt)_0$ at zero load is calculated.

In order to obtain the sample deformation rate $(dh/dt)_0$ at zero load, as shown in FIG. 3, sample deformation rates $(dh/dt)_A$, $(dh/dt)_B$, etc. at load A, load B, etc. are measured, and on the assumption that relationships between loads and sample deformation rates at the individual temperatures can approximate a straight line, an extrapolated value at zero load is calculated as the sample deformation rate $(dh/dt)_0$ at zero load.

Figure 4:
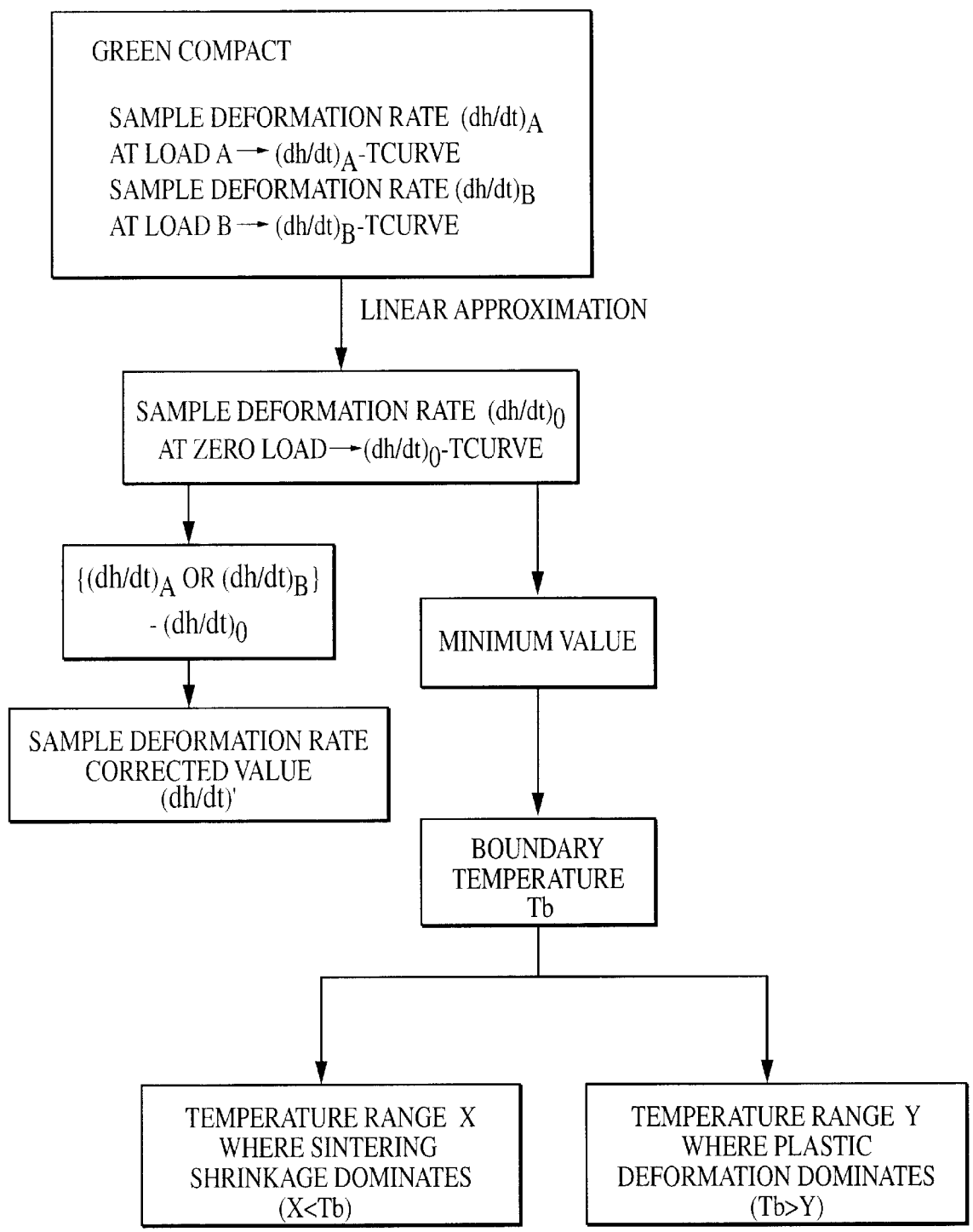
FIG. 4 is a flowchart which shows a step of extracting a corrected value of a sample deformation rate as well as a step of plotting a boundary temperature between a temperature range in which sintering shrinkage dominates and a temperature range in which plastic deformation dominates in a method for measuring the viscosity of a green compact sample in the present invention.

Specifically, as shown in a flowchart in FIG. 4, with respect to a green compact sample, a sample deformation rate $(dh/dt)_A$ at load A and a sample deformation rate $(dh/dt)_B$ at load B at temperature $T_1$ are measured. By performing linear approximation by least squares fitting using the sample deformation rate $(dh/dt)_A$ at load A and the sample deformation rate $(dh/dt)_B$ at load B, a sample deformation rate $(dh/dt)_0$ at zero load at temperature $T_1$ is calculated.

Figure 5:
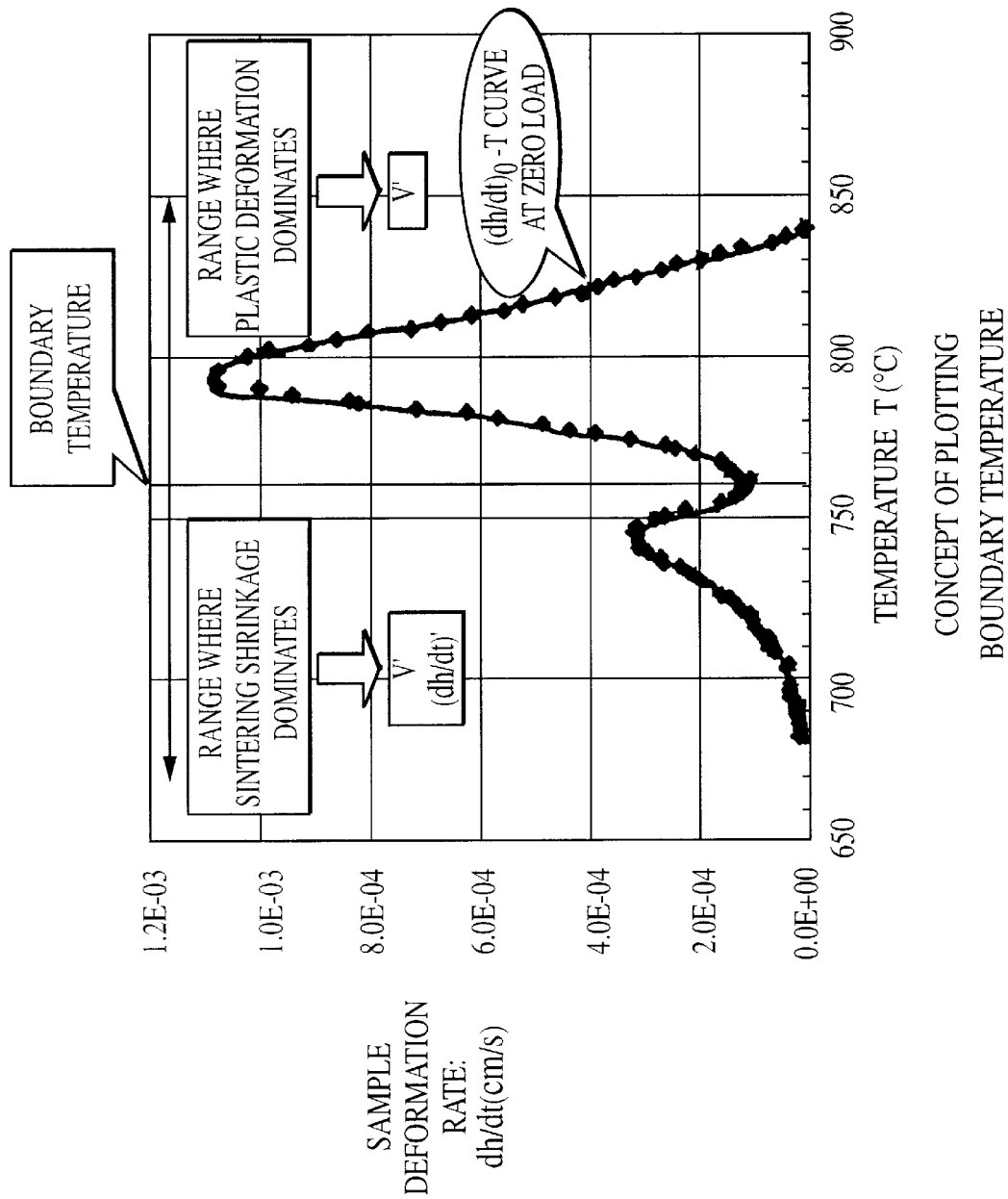
FIG. 5 is a sample deformation rate versus temperature curve which shows the plotting of a boundary temperature between the temperature range in which sintering shrinkage dominates and the temperature range in which plastic deformation dominates in a method for measuring the viscosity of a green compact sample in the present invention.

Similarly, by calculating sample deformation rates $(dh/dt)_0$ at zero load at temperatures $T_2$, $T_3$, etc., a sample deformation rate versus temperature curve ($(dh/dt)_0$–T curve) at zero load is plotted as shown in FIG. 5. Additionally, by plotting a sample deformation rate versus temperature curve at load A and a sample deformation rate versus temperature curve at load B, a sample deformation rate versus temperature curve ($(dh/dt)_0$–T curve) at zero load may be obtained for the block from the above curves.

Next, as shown in the flowchart in FIG. 4, a sample deformation rate corrected value $(dh/dt)'$ to be applied in the temperature range X in which sintering shrinkage dominates is calculated. The sample deformation rate corrected value $(dh/dt)'$ can be obtained by subtracting the sample deformation rate due to sintering shrinkage from the apparent sample deformation rate.

Specifically, a value obtained by subtracting a sample deformation rate $(dh/dt)_0$ at zero load, which corresponds to a sample deformation rate due to sintering shrinkage, from a sample deformation rate $(dh/dt)_A$ at load A or a sample deformation rate $(dh/dt)_B$ at load B, which corresponds to an apparent sample deformation rate, can be considered as a sample deformation rate corrected value $(dh/dt)'$. By repeating the above operation with respect to temperatures $T_1$, $T_2$, $T_3$, etc., the sample deformation rate corrected value $(dh/dt)'$ at each temperature is calculated.

Furthermore, as shown in the flowchart in FIG. 4, the temperature range X in which sintering shrinkage dominates and the temperature range Y in which plastic deformation dominates are separated. The separation can be performed based on the sample deformation rate versus temperature curve ($(dh/dt)_0$–T curve) at zero load shown in FIG. 5.

Specifically, as shown in FIG. 5, the minimum value at the sample deformation rate versus temperature curve ($(dh/dt)_0$–T curve) at zero load is considered as a boundary temperature $T_b$, the lower temperature side of the boundary temperature $T_b$ is set as the temperature range X in which sintering shrinkage dominates and the higher temperature side of the boundary temperature $T_b$ is set as the temperature range Y in which plastic deformation dominates.

Figure 6:
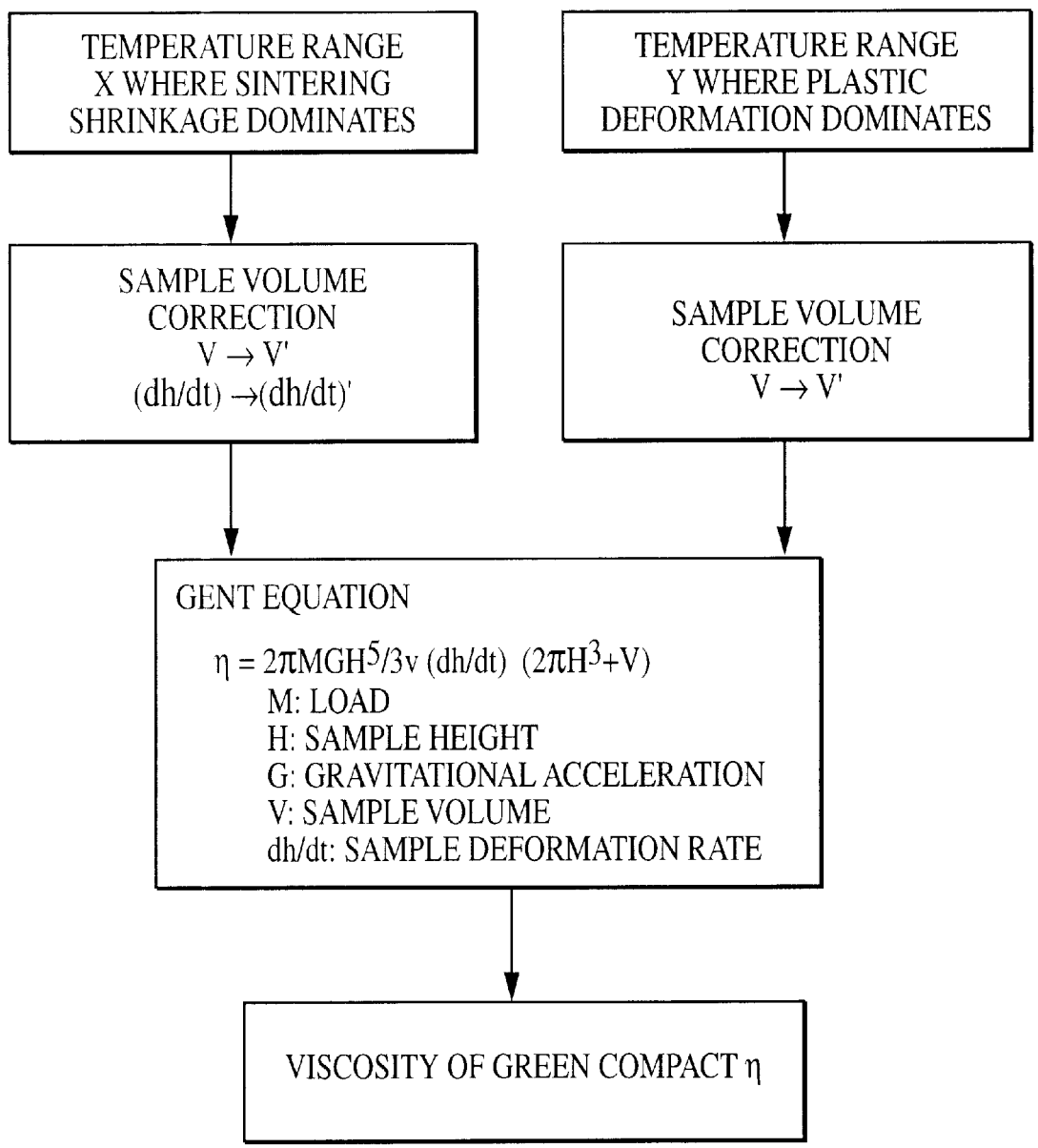
FIG. 6 is a flowchart which shows the application of a corrected value of a sample volume and a corrected value of a sample deformation rate to the Gent equation in a method for measuring the viscosity of a green compact sample in the present invention.

Next, as shown in FIG. 6, with respect to the displacement of the green compact sample, in the temperature range X in which sintering shrinkage dominates, the sample volume corrected value V' is substituted for the sample volume V and the sample deformation rate corrected value $(dh/dt)'$ is substituted for the sample deformation rate dh/dt in the Gent equation. In the temperature range Y in which plastic deformation dominates, the sample volume corrected value V' is substituted for the sample volume V in the Gent equation.

In accordance with the present invention, by such a series of operations, a viscosity-temperature curve of inorganic powder used for ceramic multilayered substrates, thick-film materials, etc. can be measured with high accuracy, and with respect to amorphous glass, crystallized glass, glass-ceramic composite materials, etc., the viscosity evaluation of a green compact sample which exhibits viscous behavior very close to that in the powder state can also be performed.

That is, in a method for measuring the viscosity of a green compact sample of the present invention, the viscosity η of a green compact sample formed by compaction molding of inorganic powder is measured in accordance with the Gent equation:

$$\eta = 2\pi M G H^5 / \{3V(dh/dt)(2\pi H^3 + V)\}$$

where M is the load, H is the height of the sample, G is the gravitational acceleration, V is the sample volume, and dh/dt is the sample deformation rate.

The method includes the steps of:

(A) finding a corrected value V' of the sample volume, where the corrected value V' of the sample volume is a volume occupied by the inorganic powder in the green compact sample;

(B) finding a corrected value $(dh/dt)'$ of the sample deformation rate, where the corrected value $(dh/dt)'$ of the sample deformation rate is the difference between the apparent sample deformation rate and the sample deformation rate due to sintering shrinkage;

(C) separating a temperature range X in which sintering shrinkage dominates and a temperature range Y in which plastic deformation dominates with respect to the displacement of the green compact sample;

(D) substituting the corrected value V' of the sample volume for the sample volume V and substituting the corrected value $(dh/dt)'$ of the sample deformation rate for the sample deformation rate dh/dt in the Gent equation with respect to the temperature range X in which sintering shrinkage dominates; and (E) substituting the corrected value V' of the sample volume for the sample volume V in the Gent equation with respect to the temperature range Y in which plastic deformation dominates.

In the method for measuring the viscosity of a green compact sample of the present invention, preferably, a sample deformation rate $(dh/dt)_A$ at load A and a sample deformation rate $(dh/dt)_B$ at load B are obtained, each as the apparent sample deformation rate, where the load A is not equal to the load B; by linear approximation using the sample deformation rate $(dh/dt)_A$ at load A and the sample deformation rate $(dh/dt)_B$ at load B, an extrapolated value at zero load is obtained as a sample deformation rate $(dh/dt)_0$ at zero load; the sample deformation rate $(dh/dt)_0$ at zero load is considered as the sample deformation rate due to sintering shrinkage; and a value obtained by subtracting the sample deformation rate $(dh/dt)_0$ at zero load from the sample deformation rate $(dh/dt)_A$ at load A or the sample deformation rate $(dh/dt)_B$ at load B is set as the corrected value $(dh/dt)'$ of the sample deformation.

However, it is desirable to obtain the sample deformation rate $(dh/dt)_0$ at zero load by linear approximation based on sample deformation rates at least three different loads, (e.g., load A, load B, and load C, where load A≠load B≠load C), because the sample deformation rate $(dh/dt)_0$ at zero load can be extracted more accurately.

In such a case, preferably, the load B is set greater than the load A, and the difference between the sample deformation rate $(dh/dt)_B$ at load B and the sample deformation rate $(dh/dt)_0$ at zero load is set as the corrected value $(dh/dt)'$ of the sample deformation rate. If the apparent sample deformation rate for calculating the corrected value $(dh/dt)'$ of the sample deformation rate is set as a sample deformation rate at a small load, variations tend to be increased when the corrected value of the sample deformation rate is extracted.

In the method for measuring the viscosity of a green compact sample of the present invention, preferably, a sample deformation rate versus temperature curve at zero load is plotted based on the sample deformation rate $(dh/dt)_0$ at zero load, the minimum value thereof is set as a boundary temperature $T_b$, the lower temperature side of the boundary temperature $T_b$ is set as the temperature range X in which sintering shrinkage dominates, and the higher temperature side of the boundary temperature $T_b$ is set as the temperature range Y in which plastic deformation dominates.

However, a method for determining the boundary temperature is not limited to the method described above, and for example, a sample deformation rate versus temperature curve for a bulk sample is plotted, and a temperature range in which a sample deformation rate versus temperature curve at zero load follows the sample deformation rate versus temperature curve for the bulk sample may be considered as the temperature range Y in which plastic deformation dominates.

Preferably, in the method for measuring the viscosity of a green compact sample of the present invention, the apparent sample deformation rate, namely the sample deformation rate $(dh/dt)_A$ at load A or the sample deformation rate $(dh/dt)_B$ at load B, is measured by a parallel plate viscometer. When the sample deformation rates at least three different loads are measured, the same parallel plate viscometer may be used. Additionally, the parallel plate viscometer is an apparatus in which a test piece (green compact sample) is placed between two parallel plates, and by heating while applying a certain load, a sample deformation rate of the test piece is detected.

In the method for measuring the viscosity of a green compact sample of the present invention, the inorganic powder may be one inorganic oxide powder selected from the group consisting of crystallized glass powder, amorphous glass powder, and glass-ceramic composite powder. By measuring the viscosity of the powder, the viscosity parameter for controlling the characteristics of ceramic multilayered substrates and thick-film materials can be accurately grasped.

Additionally, the present invention is not limited to the measurement of viscosity of a green compact sample formed by compaction molding the inorganic oxide powder, and for example, the present invention is also applicable to the measurement of viscosity for oxide ceramic powder and non-oxide ceramic powder.

Next, an apparatus for measuring the viscosity of a green compact sample of the present invention will be described.

In an apparatus for measuring the viscosity of a green compact sample, in the present invention, the viscosity $\eta$ of a green compact sample formed by compaction molding of inorganic powder is measured in accordance with the Gent equation:

$$\eta=2\pi MGH^5/\{3V(dh/dt)(2\pi H^3+V)\}$$

where M is the load, H is the height of the sample, G is the gravitational acceleration, V is the sample volume, and dh/dt is the sample deformation rate.

The apparatus includes:

(a) a sample shape measuring unit for measuring actual shape values of the green compact sample;

(b) a sample deformation rate measuring unit for measuring the apparent sample deformation rate of the green compact sample;

(c) an arithmetic processing unit for calculating the volume occupied by the inorganic powder in the green compact sample based on the actual shape values of the green compact sample and for outputting a sample volume corrected value V';

(d) an arithmetic processing unit for calculating the difference between the apparent sample deformation rate and the sample deformation rate due to sintering shrinkage of the green compact sample and for outputting a sample deformation rate corrected value $(dh/dt)'$ of the green compact sample;

(e) an arithmetic processing unit for plotting a boundary temperature between a temperature range X in which sintering shrinkage dominates and a temperature range Y in which plastic deformation dominates with respect to the displacement of the green compact sample;

(f) an arithmetic processing unit for outputting the viscosity $\eta$ in the temperature range X by substituting the sample volume corrected value V' for the sample volume V and by substituting the sample deformation rate corrected value $(dh/dt)'$ for the sample deformation rate dh/dt in the Gent equation with respect to the temperature range X in which sintering shrinkage dominates;

(g) an arithmetic processing unit for outputting the viscosity $\eta$ in the temperature range Y by substituting the sample volume corrected value V' for the sample volume V in the Gent equation with respect to the temperature range Y in which plastic deformation dominates; and (h) a display for displaying the viscosity $\eta$ in the temperature range X and the viscosity $\eta$ in the temperature range Y.

Preferably, in the apparatus for measuring the viscosity of the green compact sample of the present invention, the sample deformation rate measuring unit (b) outputs a sample deformation rate $(dh/dt)_A$ at load A and a sample deformation rate $(dh/dt)_B$ at load B, each as the apparent sample deformation rate, where the load A is not equal to the load B; and the arithmetic processing unit (d) includes:

an arithmetic processing unit for outputting an extrapolated value at zero load, i.e., a sample deformation rate $(dh/dt)_0$ at zero load, by linear approximation using the sample deformation rate $(dh/dt)_A$ at load A and the sample deformation rate $(dh/dt)_B$ at load B; and an arithmetic processing unit for outputting a value obtained by subtracting the sample deformation rate $(dh/dt)_0$ at zero load from either the sample deformation rate $(dh/dt)_A$ at load A or the sample deformation rate $(dh/dt)_B$ at load B as the sample deformation rate corrected value $(dh/dt)'$, considering the sample deformation rate $(dh/dt)_0$ at zero load as the sample deformation rate due to sintering shrinkage.

Preferably, in the apparatus for measuring the viscosity of the green compact sample of the present invention, the load B is set greater than the load A and the arithmetic processing unit (d) outputs the difference between the sample deformation rate $(dh/dt)_B$ at load B and the sample deformation rate $(dh/dt)_0$ at zero load as the sample deformation rate corrected value $(dh/dt)'$.

Preferably, in the apparatus for measuring the viscosity of the green compact sample of the present invention, the arithmetic processing unit (e) plots a sample deformation rate versus temperature curve at zero load based on the sample deformation rate $(dh/dt)_0$ at zero load, sets the minimum value thereof as a boundary temperature $T_b$, and extracts the lower temperature side of the boundary temperature $T_b$ as the temperature range X in which sintering shrinkage dominates and the higher temperature side of the boundary temperature $T_b$ as the temperature range Y in which plastic deformation dominates.

Figure 31:
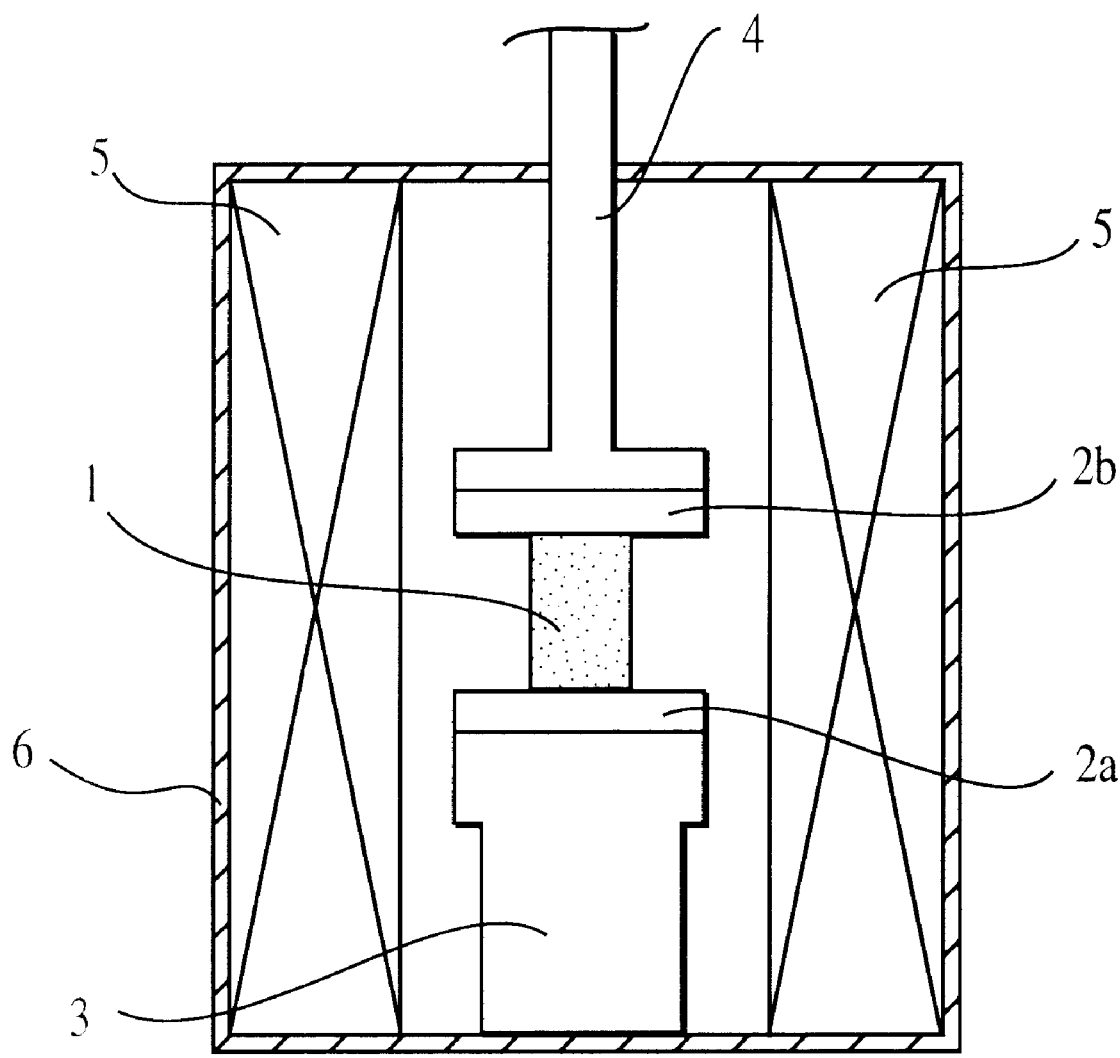
FIG. 31 is a sectional view which schematically shows a parallel plate viscometer.

Preferably, in the apparatus for measuring the viscosity of the green compact sample of the present invention, the sample deformation rate measuring unit (b) for measuring the apparent sample deformation rate is provided with a parallel plate viscometer, such as the one shown in FIG. 31.

Preferably, the apparatus for measuring the viscosity of the green compact sample of the present invention is provided with a computer including the individual arithmetic processing units described above. That is, if the computer having a program for executing a series of arithmetic processing described above, the viscosity η of the green compact sample is measured merely by inputting the sample shape values, the sample deformation rate, etc.

An outline of the apparatus for measuring the viscosity of the green compact sample of the present invention will be described with reference to FIG. 7.

Figure 7:
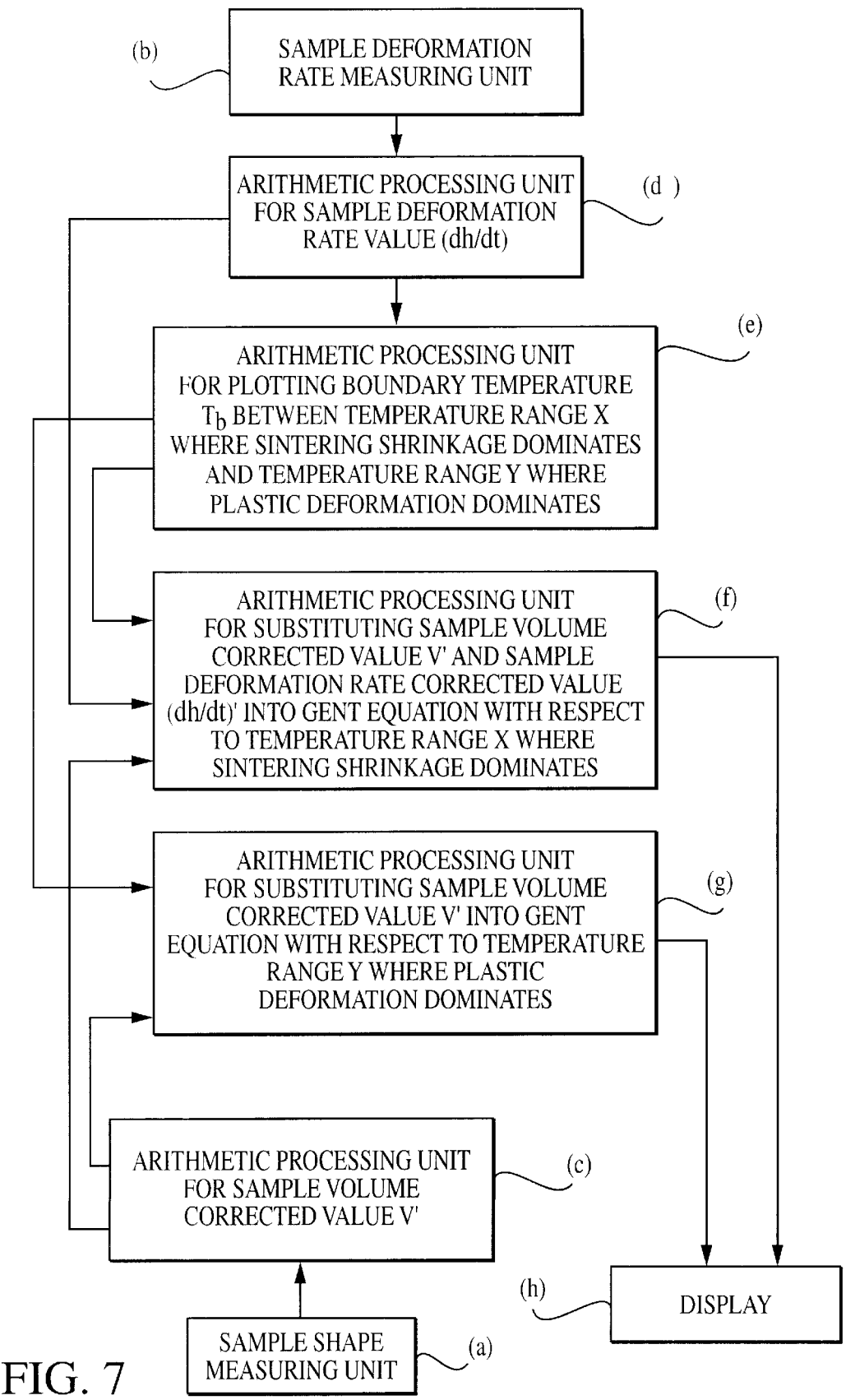
FIG. 7 is a flowchart of an apparatus for measuring the viscosity of a green compact sample in the present invention.

An apparatus for measuring the viscosity of a green compact sample shown in FIG. 7 includes:

a sample shape measuring unit (a) for measuring actual shape values, such as the height and volume of the green compact sample, the weight of inorganic powder, and the filling factor;

a sample deformation rate measuring unit (b) for measuring apparent sample deformation rates at a plurality of loads;

an arithmetic processing unit (c) for calculating a volume occupied by the inorganic powder in the green compact sample based on the actual shape values from the sample shape measuring unit and outputting a sample volume corrected value V';

an arithmetic processing unit (d) for calculating the difference between the apparent sample deformation rate based on the measured values from the sample deformation rate measuring unit and the sample deformation rate due to sintering shrinkage of the green compact sample and for outputting a sample deformation rate corrected value $(dh/dt)'$ of the green compact sample;

an arithmetic processing unit (e) for plotting a boundary temperature $T_b$ between a temperature range X in which sintering shrinkage dominates and a temperature range Y in which plastic deformation dominates with respect to the displacement of the green compact sample;

an arithmetic processing unit (f) for outputting the viscosity η in the temperature range X by substituting the sample volume corrected value V' for the sample volume V and by substituting the sample deformation rate corrected value $(dh/dt)'$ for the sample deformation rate $dh/dt$ in the Gent equation with respect to the temperature range X in which sintering shrinkage dominates;

an arithmetic processing unit (g) for outputting the viscosity η in the temperature range Y by substituting the sample volume corrected value V' for the sample volume V in the Gent equation with respect to the temperature range Y in which plastic deformation dominates; and a display (h) for displaying the viscosity η in the temperature range X and the viscosity η in the temperature range Y.

Next, an embodiment of the apparatus will be described with reference to FIG. 8.

Figure 8:
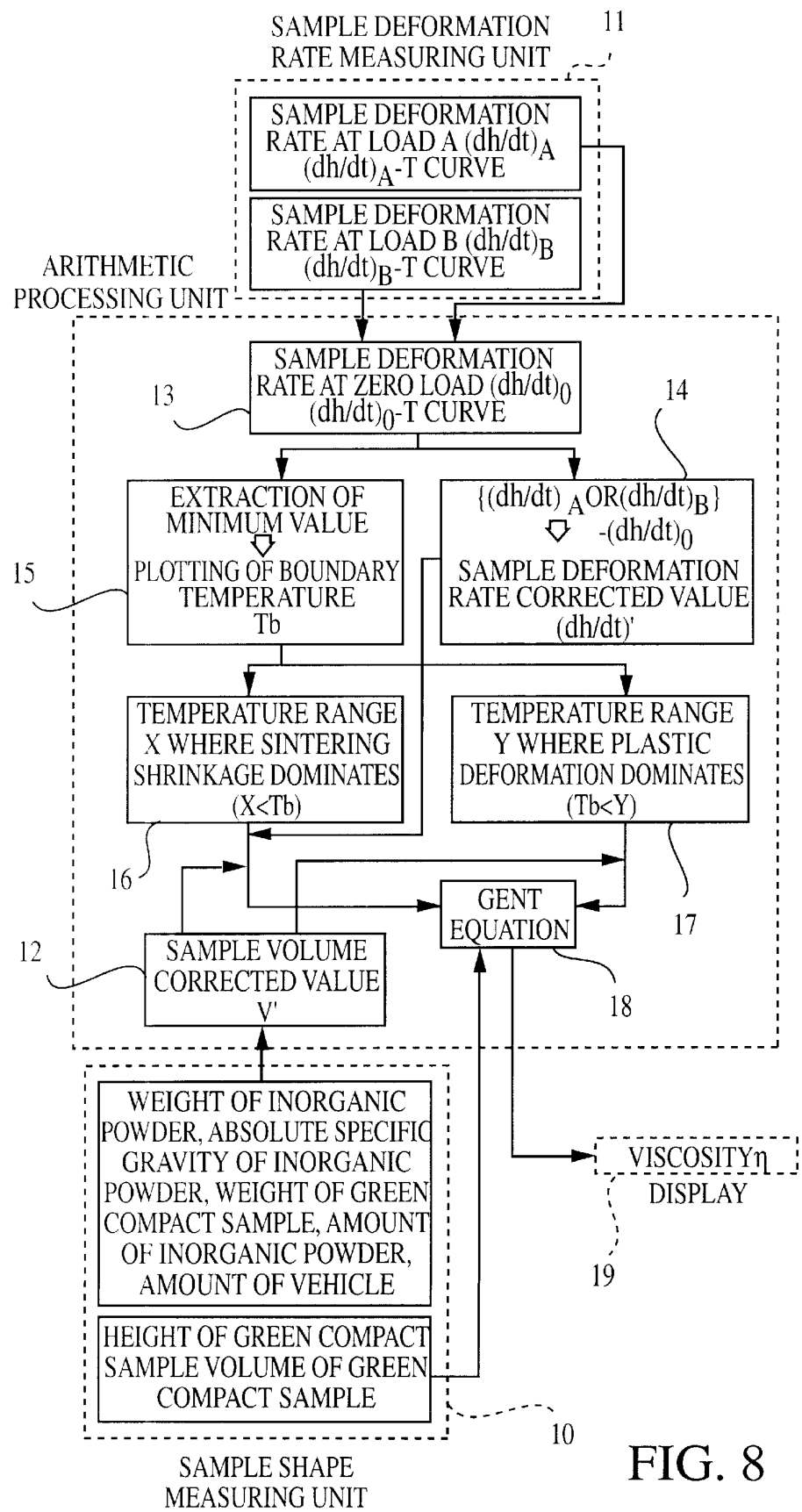
FIG. 8 is a block diagram which shows an embodiment of an apparatus for measuring the viscosity of a green compact sample in the present invention.

As shown in FIG. 8, at a sample shape measuring unit 10, the height of a green compact sample (sample height), the volume of the green compact sample (sample volume), the weight of the green compact sample (sample weight), the weight of inorganic powder, the absolute specific gravity of the inorganic powder, the amount of the inorganic powder, the amount of a vehicle, such as a binder and a solvent, etc., are accurately measured by a pycnometer, an electrobalance, etc.

On the other hand, at a sample deformation rate measuring unit 11, a sample deformation rate $(dh/dt)_A$ at load A and a sample deformation rate $(dh/dt)_B$ at load B are measured. Additionally, when a sample deformation rate measuring unit provided with a parallel plate viscometer is used, since data of the temperature and the sample height over time are outputted from the parallel plate viscometer, by processing such date, the rates $(dh/dt)_A$ and $(dh/dt)_B$ are calculated. Simultaneously, based on the measured data, a sample deformation rate versus temperature curve $\{(dh/dt)_A$–T curve$\}$ at load A and a sample deformation rate versus temperature curve $\{(dh/dt)_B$–T curve$\}$ at load B are plotted.

Next, at an arithmetic processing unit 12, based on the measured data from the sample shape measuring unit 10, the volume occupied by the inorganic powder in the green compact sample is calculated and a sample volume corrected value V' is outputted.

At an arithmetic processing unit 13, based on the measured data (or processed data) outputted from the sample deformation rate measuring unit 11, a sample deformation rate $(db/dt)_0$ at zero load is outputted. Specifically, by performing linear approximation by least squares fitting using the sample deformation rate $(dh/dt)_A$ at load A and the sample deformation rate $(dh/dt)_B$ at load B, as an extrapolated value, the sample deformation rate $(dh/dt)_0$ at zero load is outputted.

At an arithmetic processing unit 14, a value obtained by subtracting the sample deformation rate $(dh/dt)_0$ at zero load from the sample deformation rate $(dh/dt)_A$ at load A or the sample deformation rate $(dh/dt)_B$ at load B is outputted as a sample deformation rate corrected value $(dh/dt)'$.

At an arithmetic processing unit 15, based on a sample deformation rate versus temperature curve $\{(dh/dt)_0$–T curve$\}$ at zero load from the arithmetic processing unit 13, the minimum value thereof is extracted, and a temperature at which the minimum value takes place is plotted as a boundary temperature $T_b$. The lower temperature side of the boundary temperature $T_b$ as a temperature range X in which sintering shrinkage dominates and the higher temperature side of the boundary temperature $T_b$ as a temperature range Y in which plastic deformation dominates are outputted to an arithmetic processing unit 16 and an arithmetic processing unit 17, respectively.

Next, with respect to the temperature range X in which sintering shrinkage dominates, the sample volume corrected value V' from the arithmetic processing unit 12 and the sample deformation rate corrected value $(dh/dt)'$ from the arithmetic processing unit 14 are inputted to an arithmetic processing unit 18. On the other hand, with respect to the temperature range Y in which plastic deformation dominates, the sample volume corrected value V' from the arithmetic processing unit 12 is inputted to the arithmetic processing unit 18.

Next, at the arithmetic processing unit 18, with respect to the temperature range X in which sintering shrinkage dominates and the temperature range Y in which plastic deformation dominates, the individual corrected values are applied to the Gent equation as described above to calculate the viscosity $\eta$. Since the sample height H of the green compact sample is required in the Gent equation, the data thereof from the sample shape measuring unit 10 is inputted to the arithmetic processing unit 18.

The viscosity $\eta$ calculated by the arithmetic processing unit 18 is displayed at a display 19, such as a CRT or a LCD. At the display 19, the viscosity $\eta$ at each temperature may be displayed in a table form, or may be displayed as a viscosity-temperature curve.

In accordance with the apparatus for measuring the viscosity of the green compact sample of the present invention, by a series of operations described above, the viscosity of inorganic powder used for ceramic multilayered substrates, thick-film materials, and the like can be efficiently measured, and with respect to amorphous glass powder, crystallized glass powder, glass-ceramic composite powder, etc., the viscosity evaluation can be performed on the green compact sample which exhibits viscous behavior very close to that of the powder state.

Additionally, a computer readable recording medium for storing the method for measuring viscosity of a green compact sample of the present invention stores a series of steps in the method for measuring viscosity of the green compact sample of the present invention described above. Examples of the computer readable recording medium for storing the method for measuring viscosity of the green compact sample include recording media in computers, such as magnetic disks and semiconductor memories, and portable recording media, such as magnetic tapes, magnetic disks, and optical memory disks.

EXAMPLES

Formation of Sample

First, $SiO_2$—$B_2O_3$—$Al_2O_3$—CaO-based crystallized glass was formed. The composition and powder characteristics of the glass are shown in Table 2 below.

TABLE 2

| | Glass Composition | Remarks |
|---|---|---|
| Glass | $SiO_2$ 44.8 (wt %) | Crystallized glass |
| | $B_2O_3$ 10.2 (wt %) | Particle size ($D_{50}$): 1.23 μm |
| | $Al_2O_3$ 5.3 (wt %) | Specific surface area: 6.76 $m^2g^{-1}$ |
| | CaO 39.7 (wt %) | Absolute specific gravity: 2.78 $gcm^{-3}$ |

Next, an organic vehicle, such as toluene or a mixture of ethanol and isopropyl alcohol, was added to the crystallized glass having the composition shown in Table 2, and was mixed and dispersed using a ball mill. Compaction molding was performed using a press mold with a diameter of 7 mm to form cylindrical green compact samples (Sample A, Sample B, and Sample C) with a height of 8 to 8.5 mm and a diameter of 7 to 7.5 mm. With respect to Samples A, B, and C, the diameter and the height were measured by a micrometer, and the weight was measured by an electrobalance. The measurements of the shape of the samples are shown in Table 3 below.

TABLE 3

| | Diameter (mm) | Height (mm) | Weight (g) |
|---|---|---|---|
| Sample A | 7.174 | 8.031 | 0.640 |
| Sample B | 7.174 | 8.012 | 0.638 |
| Sample C | 7.175 | 8.139 | 0.647 |

For comparison, a bulk sample was formed using glass powder having the composition shown in Table 2. In order to form the bulk sample, the glass powder was poured into a platinum crucible at a melt temperature of 1,650° C., and after slow-cooling from 650° C. to room temperature, grinding was performed with a grinder to improve the parallelism of the sample. The resulting sample was a cylindrical bulk sample with a height of 6 mm and a diameter of 7 mm.

Correction of Sample Volume

Sample volume corrected values V' of Samples A, B, and C were calculated.

The sample volume corrected value V' corresponds to a value obtained by multiplying the apparent volume V of each sample by the filling factor of the crystallized glass powder. The results of the correction of the sample volume are shown in Table 4.

TABLE 4

| | V (cm3) | V' (cm3) | Filling factor (%) |
|---|---|---|---|
| Sample A | 0.325 | 0.209 | 64.5 |
| Sample B | 0.324 | 0.209 | 64.4 |
| Sample C | 0.329 | 0.212 | 64.3 |

V: Apparent volume,
V': Sample volume corrected value
(=V × Filling factor)

Correction of Sample Deformation Rate and Extraction of Boundary Temperature

Next, with respect to the green compact samples (Sample A, Sample B, and Sample C), the sample deformation rate was measured using a glass parallel plate viscometer (manufactured by Opt Corporation) having the structure shown in FIG. 31. Loads of 56.8 g, 138.8 g, and 408.8 g were applied to Samples A, B, and C, respectively, and the temperature was raised at 5° C./minute in the parallel plate viscometer. Similarly, the sample deformation rate of the bulk sample was measured at a load of 138.8 g. The measurement results of the sample deformation rate at each temperature are shown in FIG. 9.

With respect to Sample A (Load: 56.8 g), Sample B (Load: 138.8 g), and Sample C (Load: 408.8 g), the extrapolated value at zero load by linear approximation by least squares fitting, i.e., the sample deformation rate $(dh/dt)_0$ at zero load was calculated. The sample deformation rate $(dh/dt)_0$ at zero load at each temperature is also shown in FIG. 9.

Figure 9:
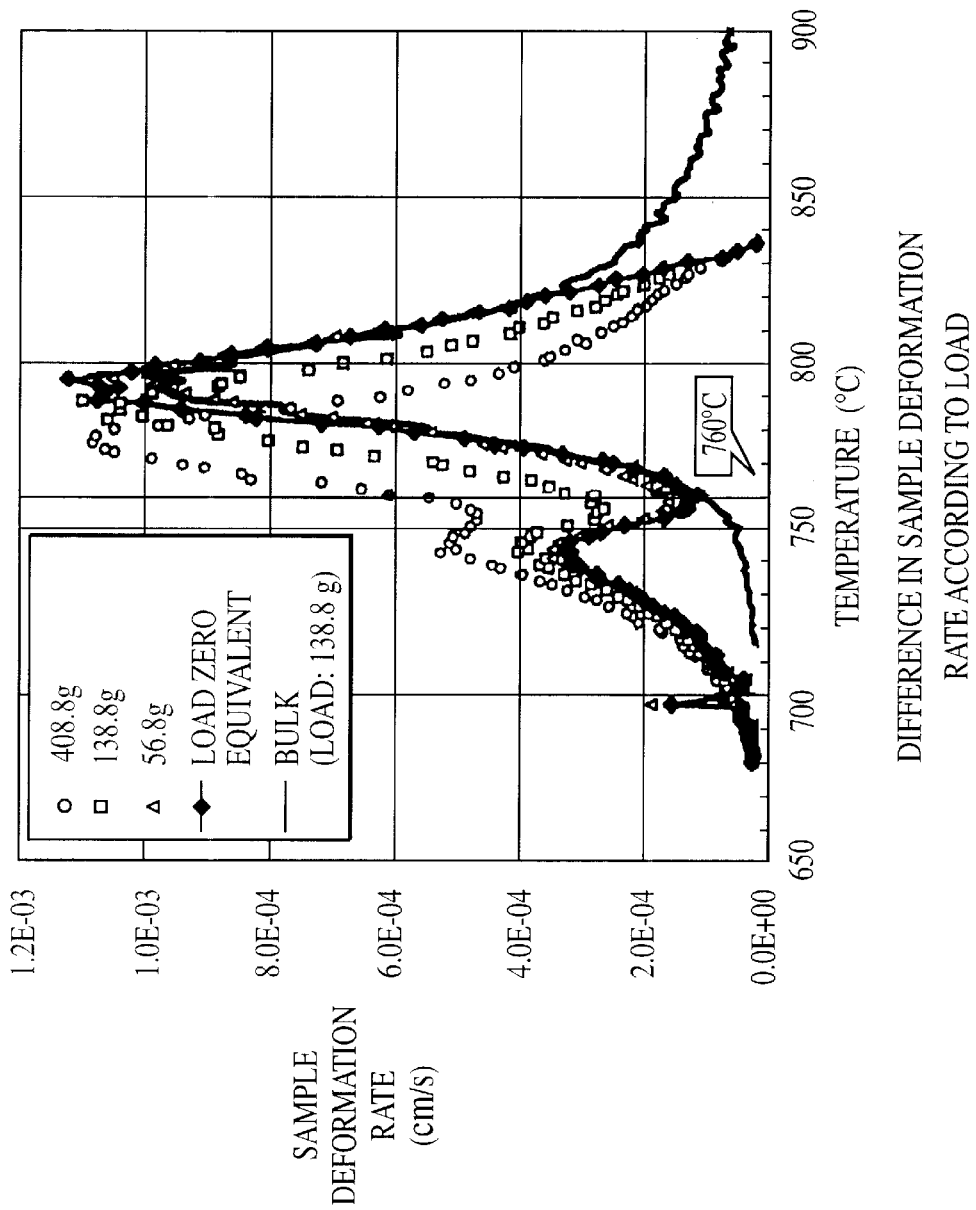
FIG. 9 is a graph illustrating sample deformation rate versus temperature curves which show a difference in sample deformation rate according to the load in a first embodiment of the present invention.

As shown in FIG. 9, although there is a large difference between the sample deformation rate $(dh/dt)_0$ at zero load and the sample deformation rate of the bulk sample up to approximately 760° C., at approximately 760° C. to 830° C., both sample deformation rates substantially agree. Additionally, both sample deformation rates do not agree at approximately 830° C. or more because the green compact sample is crystallized and the sample deformation rate at zero load does not follow the sample deformation rate of the bulk sample.

Consequently, a range up to 760° C. is believed to be a temperature range X in which sintering shrinkage dominates. Therefore, the sample deformation rate $(dh/dt)_0$ at zero load can be considered as the deformation rate due to sintering shrinkage. In the range up to 760° C., a value obtained by subtracting the sample deformation rate $(dh/dt)_0$ at zero load from the measured apparent sample deformation rate of the green compact sample (i.e., the sample deformation rate of Sample A, Sample B, or Sample C) is set as a sample deformation rate corrected value V'.

As the load increases, the influence of viscous flow on the sample deformation rate increases and the influence of the load on sintering shrinkage decreases, and therefore, herein, a value obtained by subtracting the sample deformation rate at zero load from the sample deformation rate of Sample C (load: 408.8 g) is set as the sample deformation rate corrected value (dh/dt)'.

In the range at 760° C. or more (up to 830° C.), the sample deformation rate $(dh/dt)_0$ at zero load approximates the sample deformation rate of the bulk sample, and thus this range is believed to be a temperature range in which plastic deformation due to viscous flow dominates. However, as is obvious from FIG. 9, as the load is increased, the sample deformation rate versus temperature curve shifts to the lower temperature side, while at a load of 56.8 g, the behavior substantially agrees with that of zero load. Although sample deformation under the influence of the load (i.e., the effect of acceleration of sintering by the load) appears to be added to plastic deformation if the load is increased, since the load is taken into consideration in the Gent equation, the effect is believed to be reflected in the viscosity value.

Accordingly, herein, the boundary temperature is set at 760° C., and the lower temperature side of 760° C. is set as the temperature range X in which sintering shrinkage dominates and the higher temperature side of 760° C. is set as the temperature range Y in which plastic deformation dominates. Additionally, the minimum value of the sample deformation rate versus temperature curve at zero load shown in FIG. 9 agrees with the boundary temperature, and clearly, the minimum value of the sample deformation rate versus temperature curve at zero load corresponds to the boundary temperature between the temperature range X in which sintering shrinkage dominates and the temperature range Y in which plastic deformation dominates.

Calculation of Viscosity (Application of Gent Equation)

Next, by applying the sample volume corrected value V' and the sample deformation rate corrected value (dh/dt)' in the Gent equation, the viscosity of each sample is measured.

That is, in the temperature range X in which sintering shrinkage dominates, the sample volume corrected value V' is substituted for the sample volume V and the sample deformation rate corrected value (dh/dt)' is substituted for the sample deformation rate dh/dt in the Gent equation. In the temperature range Y in which plastic deformation dominates, the sample volume corrected value V' is substituted for the sample volume V in the Gent equation.

Figure 10:
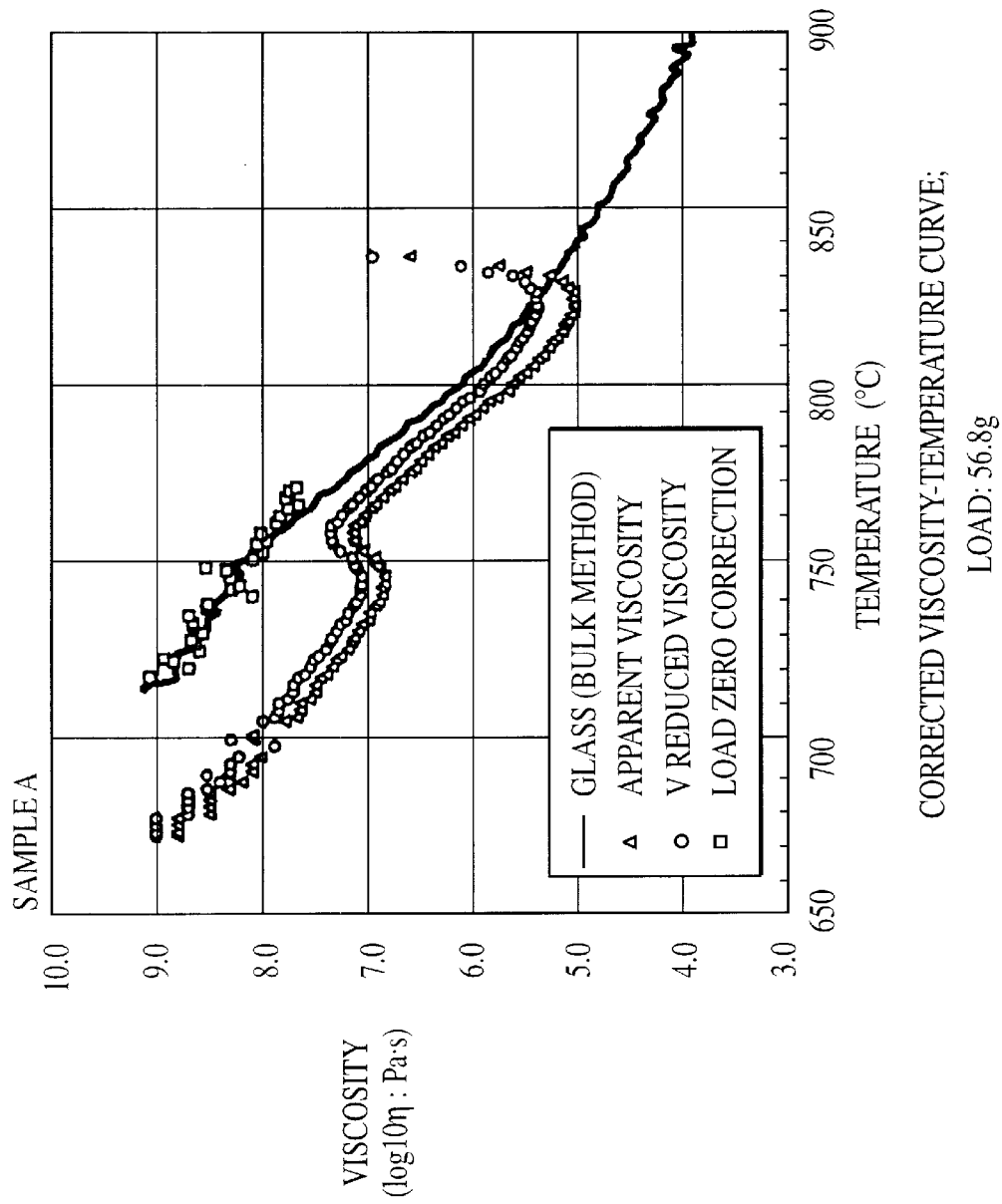
FIG. 10 is a graph showing a viscosity-temperature curve of Sample A (load: 56.8 g) in the first embodiment of the present invention.
Figure 11:
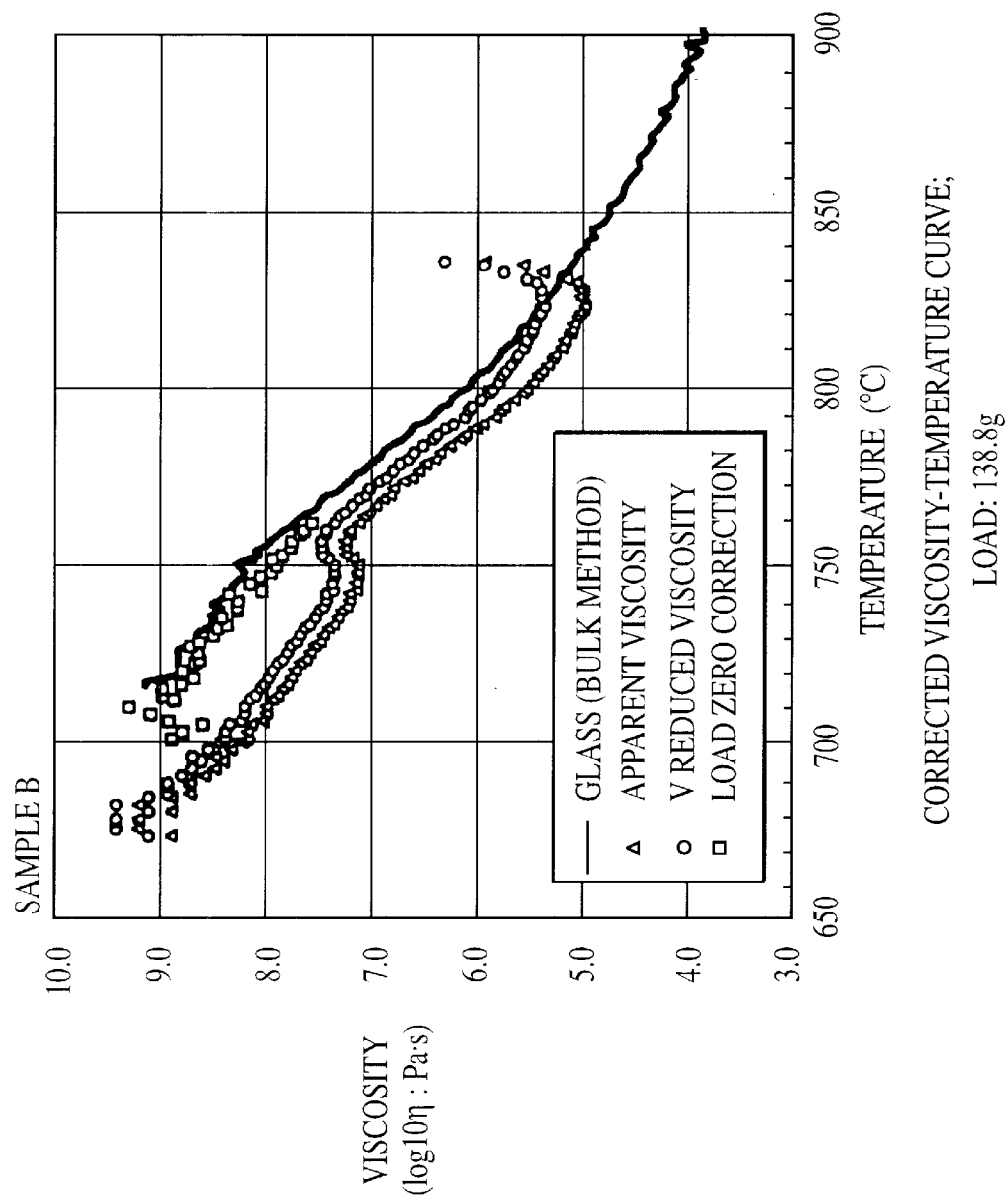
FIG. 11 is a graph showing a viscosity-temperature curve of Sample B (load: 138.8 g) in the first embodiment of the present invention.
Figure 12:
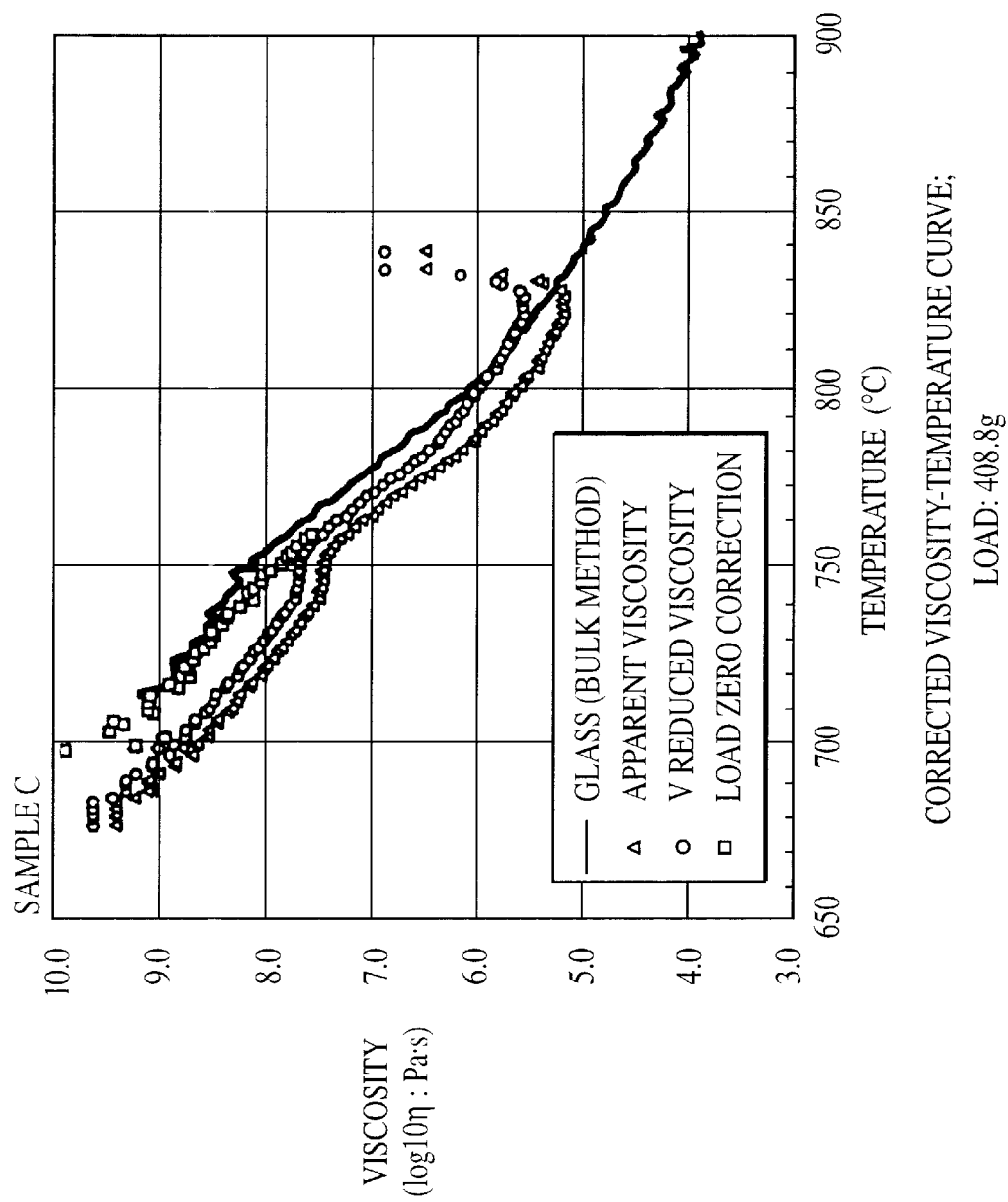
FIG. 12 is a graph showing a viscosity-temperature curve of Sample C (load: 408.8 g) in the first embodiment of the present invention.

FIGS. 10 to 12 show viscosity-temperature curves plotted according to the Gent equation. FIG. 10 shows the viscosity-temperature curve for Sample A (load: 56.8 g), FIG. 11 shows the viscosity-temperature curve for Sample B (load: 138.8 g), and FIG. 12 shows the viscosity-temperature curve for Sample C (load: 408.8 g).

Table 5 below shows the relationships between the temperature range X in which sintering shrinkage dominates, the temperature range Y in which plastic deformation dominates, and raw data values (applied in the Gent equation without correction) with respect to Sample A (load: 56.8 g), Sample B (load: 138.8 g), and Sample C (load: 408.8 g), the temperature of the bulk sample, and the viscosity.

TABLE 5

| Viscosity | Sample A (Load 56.8 g) | | | Sample B (Load 138.8 g) | | | Sample C (Load 408.8 g) | | | Bulk sample |
|---|---|---|---|---|---|---|---|---|---|---|
| | Temperature range X | Temperature range Y | Raw data | Temperature range X | Temperature range Y | Raw data | Temperature range X | Temperature range Y | Raw data | |
| 8.0 | 753 | — | 696 | 746 | — | 709 | 749 | — | 722 | 755 |
| 7.0 | — | 770 | 763 | — | 771 | 766 | — | 771 | 765 | 779 |
| 6.5 | — | 783 | 778 | — | 783 | 778 | — | 782 | 776 | 790 |
| 6.0 | — | 796 | 796 | — | 796 | 789 | — | 800 | 789 | 802 |
| 5.5 | — | 813 | 803 | — | 818 | 801 | — | 822 | 805 | 820 |

Viscosity: log η (Pa.s)

As is obvious from FIGS. 10 to 12 and Table 5, in the temperature range X in which sintering shrinkage dominates, by substituting the sample volume corrected value V' for the sample volume V and by substituting the sample deformation rate corrected value (dh/dt)' for the sample deformation rate dh/dt, and in the temperature range Y in which plastic deformation dominates, by substituting the sample volume corrected value V' for the sample volume V in the Gent equation, it was possible to narrow the differences from the measurements of viscosity of the bulk sample to approximately 5° C. to 10° C. Additionally, by further correcting the treatment of the sample volume (the initial value) and other error factors, the viscous behavior may be further approximated to that of the bulk sample.

Figure 13:
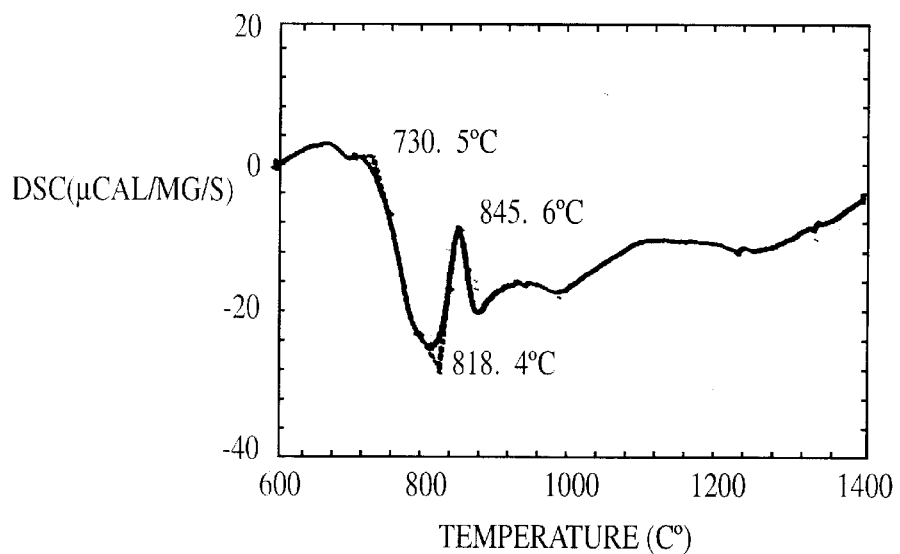
FIG. 13 is a graph showing the results of differential scanning calorimetry (DSC) with respect to a green compact sample in the first embodiment of the present invention.
Figure 14:
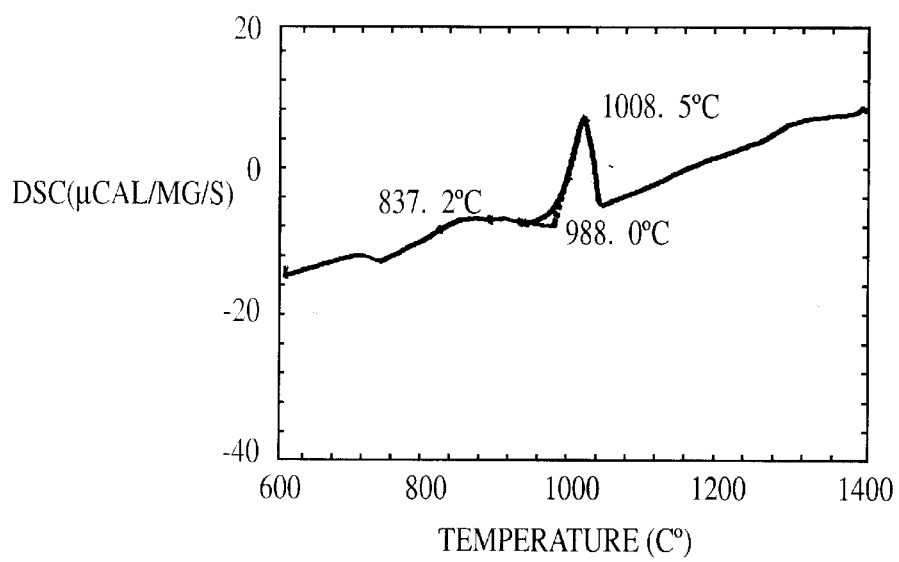
FIG. 14 is a graph showing the results of DSC with respect to a bulk sample in the first embodiment of the present invention.

As is also obvious from FIGS. 10 to 12 and Table 5, with respect to the bulk sample, an increase in viscosity due to crystallization, which was observed in the green compact sample, was not observed. The increase in viscosity in the green compact sample substantially corresponded to the crystallization temperature $T_c$ as shown in the results of DSC in FIGS. 13 and 14.

In short, by making the corrections summarized below in the Gent equation, it was possible to efficiently measure the viscosity of the green compact sample with high accuracy.

(1) Separation of the temperature range X in which sintering shrinkage dominates and the temperature range Y in which plastic deformation dominates with respect to the displacement of the green compact sample, i.e., the separation of the deformation rate due to sintering shrinkage and the deformation rate due to plastic deformation included in the sample deformation rate (measured value).

(2) Correction of the sample volume and correction of the sample deformation rate in the temperature range X in which sintering shrinkage dominates.

(3) Correction of the sample volume in the temperature range Y in which plastic deformation dominates.

As described above, in accordance with the method for measuring the viscosity of the green compact sample, with respect to the viscosity of the green compact sample formed by compaction molding of inorganic powder, such as crystallized glass powder, amorphous glass powder, or glass-ceramic composite powder, since the measurement is performed according to the steps described above, the viscous behavior of the green compact sample can be evaluated and measured with high accuracy, in particular, in the intermediate viscosity region of $10^4$ to $10^9$ Pa·s, which is particularly important in the sintering process, etc.

In accordance with the apparatus for measuring the viscosity of the green compact sample, with respect to the viscosity of the green compact sample formed by compaction molding of inorganic powder, since the apparatus is provided with the sample shape measuring unit, the sample deformation rate measuring unit, and the individual arithmetic processing units, the viscous behavior of the green compact sample can be efficiently measured.

The computer readable recording medium for storing the method for measuring the viscosity of the green compact sample described above is used in the present invention, and it is possible to store the method for measuring the viscosity of the green compact sample in the present invention and to easily transfer the technology thereof, facilitating the use thereof by many people.

Second Embodiment

In a method for measuring the viscosity of a green compact sample in the present invention, in which the viscosity η of a green compact sample formed by compaction molding of inorganic powder is measured in accordance with the Gent equation:

$$=2\pi MGH^5/\{3V(dh/dt)(2\pi H^3+V)\}$$

where M is the load, H is the height of the sample, G is the gravitational acceleration, V is the sample volume, and dh/dt is the sample deformation rate, the measurement is performed using the green compact sample which is preliminarily calcined so that particles of the inorganic powder are sufficiently brought into close contact with each other. The calcination may be performed with respect to the green compact sample or the inorganic powder.

In the method for measuring the viscosity of the green compact sample of the present invention, preferably, the inorganic powder is one inorganic oxide powder selected from the group consisting of amorphous glass powder, crystallized glass powder, and glass-ceramic composite powder. More preferably, amorphous glass powder is used as the inorganic powder. Since the amorphous glass powder exhibits reversible characteristics during heating and cooling in the calcining process, a relatively wide range of conditions can be employed for the calcining temperature, the calcining time, the rate of temperature rise, etc.

In the method for measuring the viscosity of the green compact sample of the present invention, preferably, the calcination is performed at the softening point or less of the inorganic powder. That is, by calcining the inorganic powder, such as amorphous glass powder, crystallized glass powder, or glass-ceramic composite powder, at the softening point or less for a predetermined period of time so that particles thereof are sufficiently brought into close contact with each other, the viscous behavior of the green compact sample after the calcination can become very close to that of an incompressible fluid.

Accordingly by merely applying the measured values of the sample volume and the sample height of the calcined green compact sample and the measured value (or the calculated value) of the sample deformation rate by a parallel plate viscometer, etc. in the Gent equation, the viscosity of the green compact sample can be measured with high accuracy.

Preferably, the calcination is performed at T−10° C., or more, where T is the softening point (° C.) of the inorganic powder, i.e., at the softening point minus 10° C., or more. That is, if the calcination is performed so as to satisfy the relationship, T−10≦t≦T, where t is the calcining temperature, particles can be sufficiently brought into close contact with each other and sample deformation due to softening flow does not occur, and thus the viscosity of the green compact sample can be measured with high accuracy.

Next, the method for measuring the viscosity of the green compact sample of the present invention will be described with reference to the flowchart in FIG. 15.

Figure 15:
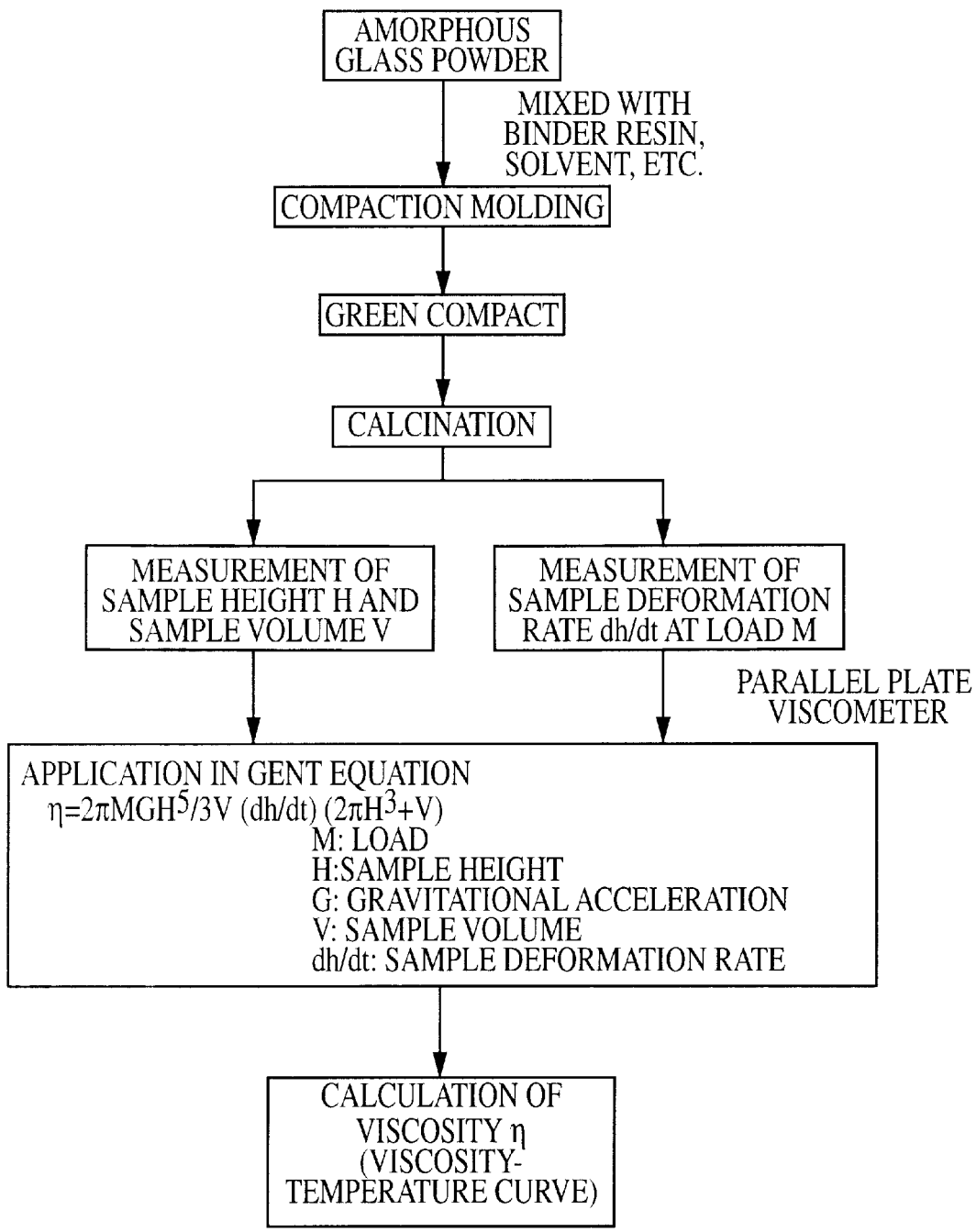
FIG. 15 is a flowchart showing an embodiment of a method for measuring the viscosity of a green compact sample in the present invention.

As shown in FIG. 15, first, amorphous glass powder is formed by a high-temperature melting method, a sol-gel process, or the like. The amorphous glass powder is mixed with a vehicle composed of an organic binder (or a water-based binder), a solvent, etc. and is dispersed. The resultant mixture is subjected to compaction molding to form a green compact sample composed of the amorphous glass.

The green compact sample is then calcined at an appropriate temperature to sufficiently bring powder particles into close contact with each other. The appropriate temperature for sufficiently bringing particles of the amorphous glass powder into close contact with each other, preferably, is the softening point or less, and more preferably, is in the range from the softening point minus 10° C. up to the softening point.

That is, in the present invention, as long as the calcination is performed under the conditions to sufficiently bring powder particles into close contact with each other, the calcining temperature, the rate of temperature rise, etc., are not particularly limited. For example, in the case of a green compact sample composed of amorphous glass powder, the calcining time may be set at approximately 30 to 90 minutes, and the temperature may be raised by approximately 1 to 10° C./minute.

With respect to the calcined green compact sample, the sample height H and the sample volume V are measured, and also by using a parallel plate viscometer as shown in FIG. 31, the sample height H is measured over time as the temperature is gradually increased while load M is being applied, and the sample deformation rate dh/dt is calculated based on the measurements.

The measured sample height H, sample volume V, and sample deformation rate dh/dt are applied in the Gent equation to find the viscosity η (viscosity-temperature curve) of the green compact sample.

By calcining the green compact sample before measuring with the parallel plate viscometer, the viscosity η of the amorphous glass powder used for ceramic multilayered substrates, thick-film materials, etc., and the viscosity-temperature curve can be measured with high accuracy. That is, with respect to amorphous glass powder, the viscosity of the green compact sample which exhibits viscous behavior very close to that in the powder state can be evaluated.

Although the method for measuring the viscosity of the green compact sample has been described with respect to amorphous glass powder, the present invention is not limited to the measurement of the viscosity of the green compact sample comprising the amorphous glass powder.

For example, by applying the present invention to crystallized glass power, glass-ceramic composite powder, or other inorganic powder, in a manner similar to that described above, the viscosity η thereof can be evaluated with high accuracy, and also the viscosity-temperature curve thereof can be plotted with high accuracy. However, when the present invention is applied to crystallized glass powder or glass-ceramic composite powder, the rate of temperature rise is preferably set as low as possible, for example, at 1 to 5° C./minute. This is because of the fact that seeds of precipitating crystals can be sufficiently formed.

Additionally, in the present invention, although the calcined green compact sample exhibits viscous behavior very close to that of an incompressible fluid, depending on the remaining state of the binder in the green compact sample, etc., viscous behavior slightly different therefrom may be exhibited. In such a case, as described below, the Gent equation may be corrected.

That is, as described above, the Gent equation is only applicable in a case where a test piece can be assumed to be an incompressible fluid. In contrast, in the green compact sample, which is formed by compaction molding of the inorganic powder and the vehicle, a change in volume may occur due to evaporation of the binder, etc. as firing advances.

In order to correct the change in volume, first, a volume obtained by multiplying the apparent volume of the green compact sample by the filling factor of the inorganic powder in the green compact sample is considered as a corrected value V' of the sample volume, and the corrected value V' is substituted into the Gent equation. The filling factor of the inorganic powder can be easily calculated based on the absolute specific gravity of the inorganic powder, the compositional ratio, and the weight of the green compact sample according to the correction of the Gent equation which has been described with reference to FIGS. 2 to 6 in the first embodiment.

In accordance with the present invention, by such a series of operations, a viscosity-temperature curve of amorphous glass powder as well as that of crystallized glass powder, glass-ceramic composite powder, or the like can be measured with higher accuracy.

That is, the method for measuring the viscosity of a green compact sample in the second embodiment may include the steps of:

(A) finding a corrected value V' of the sample volume of the calcined green compact sample, where the corrected value V' of the sample volume is a volume occupied by the inorganic powder in the green compact sample;

(B) finding a corrected value (dh/dt)' of the sample deformation rate of the calcined green compact sample, where the corrected value (dh/dt)' of the sample deformation rate is the difference between the apparent sample deformation rate and the sample deformation rate due to sintering shrinkage;

(C) separating a temperature range X in which sintering shrinkage dominates and a temperature range Y in which plastic deformation dominates with respect to the displacement of the calcined green compact sample;

(D) substituting the corrected value V' of the sample volume for the sample volume V and substituting the corrected value (dh/dt)' of the sample deformation rate for the sample deformation rate dh/dt in the Gent equation with respect to the temperature range X in which sintering shrinkage dominates; and (E) substituting the corrected value V' of the sample volume for the sample volume V in the Gent equation with respect to the temperature range Y in which plastic deformation dominates.

Preferably, a sample deformation rate $(dh/dt)_A$ at load A and a sample deformation rate $(dh/dt)_B$ at load B are obtained, each as the apparent sample deformation rate, where the load A is not equal to the load B, by performing linear approximation using the sample deformation rate $(dh/dt)_A$ at load A and the sample deformation rate $(dh/dt)_B$ at load B, an extrapolated value at zero load is obtained as a sample deformation rate $(dh/dt)_0$ at zero load, the sample deformation rate $(dh/dt)_0$ at zero load is considered as the sample deformation rate due to sintering shrinkage, and a value obtained by subtracting the sample deformation rate $(dh/dt)_0$ at zero load from the sample deformation rate $(dh/dt)_A$ at load A or from the sample deformation rate $(dh/dt)_B$ at load B is set as the corrected value $(dh/dt)'$ of the sample deformation.

However, it is desirable to obtain the sample deformation rate $(dh/dt)_0$ at zero load by linear approximation based on sample deformation rates at least three different loads (e.g., load A, load B, and load C, where load A≠load B≠load C), because the sample deformation rate $(dh/dt)_0$ at zero load can be extracted more accurately.

In such a case, preferably, the load B is set greater than the load A, and a difference between the sample deformation rate $(dh/dt)_B$ at load B and the sample deformation rate $(dh/dt)_0$ at zero load is set as the corrected value $(dh/dt)'$ of the sample deformation rate. If the apparent sample deformation rate for calculating the corrected value $(dh/dt)'$ of the sample deformation rate is set as a sample deformation rate at a small load, variations tend to be increased when the corrected value of the sample deformation rate is extracted.

In the present invention, preferably, a sample deformation rate versus temperature curve at zero load is plotted based on the sample deformation rate $(dh/dt)_0$ at zero load, the minimum value thereof is set as a boundary temperature $T_b$, the lower temperature side of the boundary temperature $T_b$ is set as a temperature range X in which sintering shrinkage dominates, and the higher temperature side of the boundary temperature $T_b$ is set as a temperature range Y in which plastic deformation dominates.

However, a method for determining the boundary temperature is not limited to the method described above, and for example, a sample deformation rate versus temperature curve for a bulk sample is plotted, and a temperature range in which a sample deformation rate versus temperature curve at zero load follows the sample deformation rate versus temperature curve for the bulk sample maybe considered as the temperature range Y in which plastic deformation dominates.

EXAMPLES

First, amorphous glass powders represented by Sample 1, Sample 2, and Sample 3 were formed by a high-temperature melting method. The composition, thermal characteristics, powder characteristics, etc. of Samples 1, 2, and 3 are shown in Table 6 below.

TABLE 6

| | Glass composition (mol %) | | Thermal characteristics | Remarks |
|---|---|---|---|---|
| Sample 1 | PbO | 32.79 | Glass transition | Amorphous glass |
| | $B_2O_3$ | 28.07 | point (Tg) | Particle size ($D_{50}$): 2.84 μm |
| | ZnO | 26.66 | → 403° C. | Specific surface area: |
| | $SiO_2$ | 8.12 | Softening point | 1.62 $m^2g^{-1}$ |
| | $Al_2O_3$ | 2.20 | ($10^{7.6}$ Pa.s) | Absolute specific gravity: |
| | BaO | 2.11 | → 454° C. | 5.27 |
| | MgO | 0.03 | | |
| | $Na_2O$ | 0.01 | | |
| Sample 2 | PbO | 46.12 | Glass transition | Amorphous glass |
| | $B_2O_3$ | 35.78 | point (Tg) | Particle size ($D_{50}$): 2.09 μm |
| | ZnO | 8.92 | → 381° C. | Specific surface area: |
| | $SiO_2$ | 5.69 | Softening point | Unmeasurable |
| | $Al_2O_3$ | 3.49 | ($10^{7.6}$ Pa.s) | Absolute specific gravity: |
| | | | → 427° C. | 5.41 |
| Sample 3 | $B_2O_3$ | 37.42 | Glass transition | Amorphous glass |
| | ZnO | 38.57 | point (Tg) | Particle size ($D_{50}$): 5.02 μm |
| | $SiO_2$ | 9.53 | → 477° C. | Specific surface area: |
| | $Li_2O$ | 9.43 | Softening point | 1.92 $m^2g^{-1}$ |
| | CaO | 5.05 | ($10^{7.6}$ Pa.s) | Absolute specific gravity: |
| | | | → 558° C. | 3.16 |

Next, a water-based vehicle (vinyl acetate-based vehicle) was added to the amorphous glass powders of Samples 1, 2, and 3, and was mixed and dispersed using a ball mill. Compaction molding was performed using a press mold with a diameter of 7 mm to form cylindrical green compact samples with a height of 8 to 8.5 mm and a diameter of 7 to 7.5 mm.

With respect to the green compact samples composed of the individual amorphous glass powders of Samples 1 to 3, calcination was performed at a temperature in the vicinity of the softening point using an electric furnace, and the diameter and the height of the calcined green compact samples were measured by a micrometer. Additionally, in the calcination, the temperature was raised from room temperature to the calcining temperature at 3° C./minute, and after maintaining the calcining temperature for 1 hour, the green compact samples were left to cool to room temperature.

For comparison, bulk samples were formed using the amorphous glass powders having the compositions shown in Table 6. In order to form the bulk samples, each amorphous glass powder was poured into a platinum crucible and melted. After slow-cooling to room temperature, grinding was performed with a grinder to improve the parallelism of the bulk. The resulting sample was a cylindrical bulk sample with a height of 6 mm and a diameter of 7 mm.

Next, with respect to the green compact samples of Samples 1 to 3, the sample deformation was measured using a parallel plate viscometer (manufactured by Opt Corporation) having the structure shown in FIG. 31, and viscosity-temperature curves were plotted according to the procedure described above. A load of 138.8 g was applied to each sample, and the temperature was raised by 5° C./minute when the sample deformation was measured by the parallel plate viscometer. Similarly, the viscosity-temperature curves of the bulk samples were also plotted.

The calcination was performed under the nine conditions below with respect to each of the green compact samples and the bulk samples of Samples 1 to 3.

(1) Softening point plus 50° C.
(2) Softening point plus 30° C.
(3) Softening point plus 20° C.
(4) Softening point plus 10° C.
(5) Softening point
(6) Softening point minus 10° C
(7) Softening point minus 20° C.
(8) Softening point minus 30° C.
(9) Softening point minus 50° C.

For comparison, measurements were also performed with respect to green compact samples without calcining.

As a result, with respect to either green compact sample of Samples 1 to 3, when calcination was performed at a temperature higher than the softening point, under the conditions of (1) to (4), the occurrence of sample deformation was occasionally observed. That is, when calcination was performed at a temperature that was higher than the softening point of the amorphous glass, the glass powder in the green compact sample occasionally softened and flowed, thus being unable to maintain the sample shape of the green compact sample. Consequently, the calcining temperature is preferably set at the softening point or less.

Figure 16:
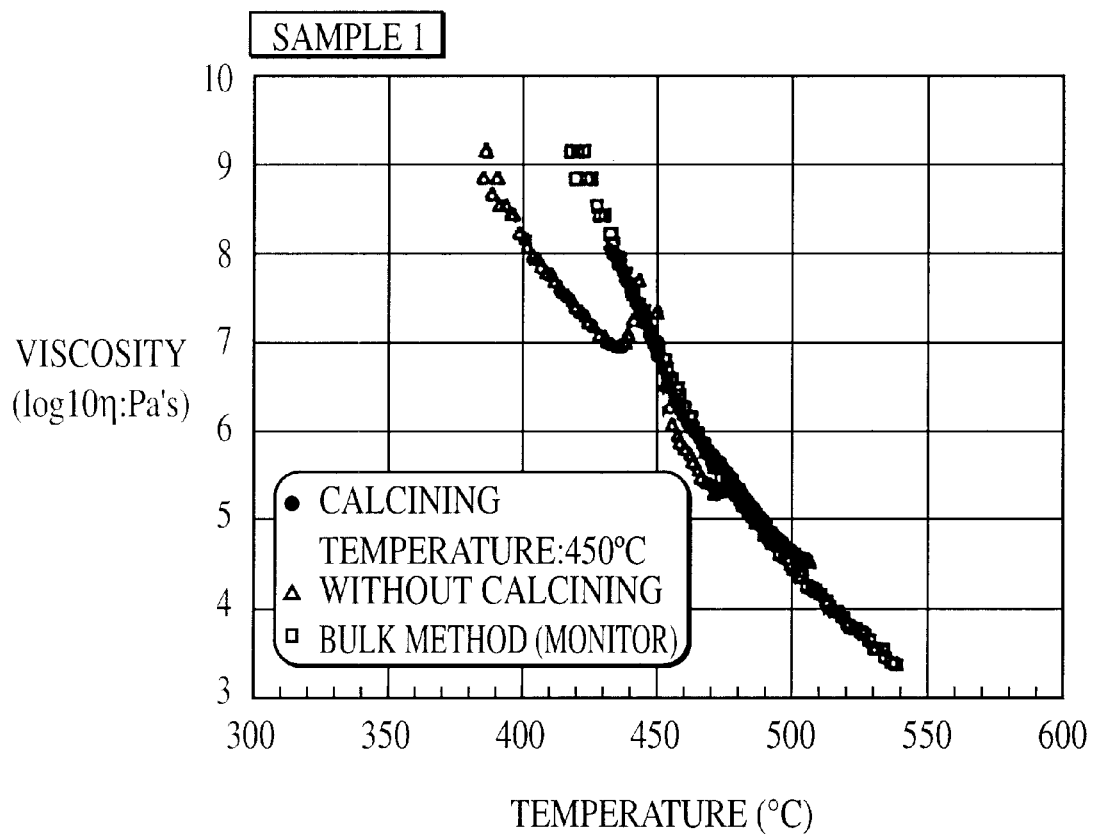
FIG. 16 is a graph showing a viscosity-temperature curve when a green compact sample of Sample 1 is calcined at the softening point in a second embodiment of the present invention.
Figure 17:
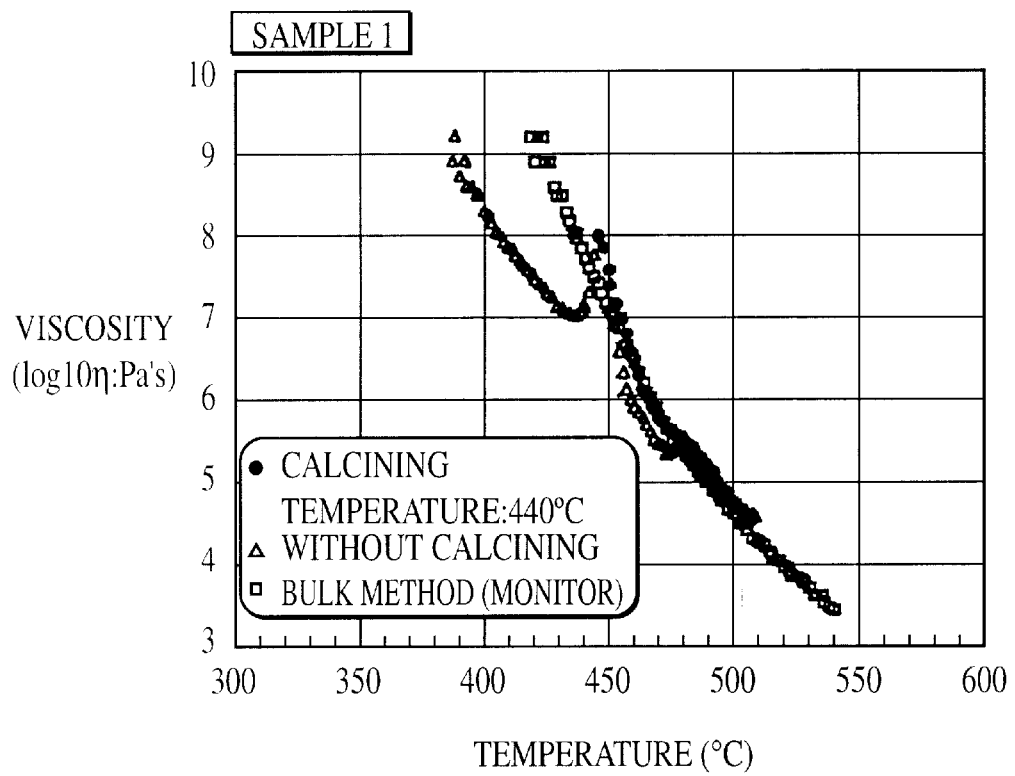
FIG. 17 is a graph showing a viscosity-temperature curve when a green compact sample of Sample 1 is calcined at the softening point minus 10° C. in the second embodiment of the present invention.

With respect to the green compact sample of Sample 1, when calcination was performed at the softening point, i.e., at 450° C., under the condition (5), as shown in FIG. 16, the viscosity-temperature curve indicated by ● for the calcined sample was close to the viscosity-temperature curve indicated by □ for the bulk sample. The reason for this is believed to be that since powder particles were sufficiently brought into close contact with each other in the green compact sample at the softening point, i.e., at 450° C., the viscous behavior thereof was very close to that of an incompressible fluid. When the calcination was performed at the softening point minus10° C. (440° C.) under the condition (6), as shown in FIG. 17, the viscosity-temperature curve indicated by ● for the calcined sample was also close to the viscosity-temperature curve indicated by ∇ for the bulk sample. The reason for this is believed to be that since powder particles were sufficiently brought into close contact with each other in the green compact sample even at the softening point minus 10° C., i.e., at 440° C., the viscous behavior thereof was very close to that of an incompressible fluid. Additionally, as a guideline for viscosity in this method, a difference in temperature of 2% or less between the calcined green compact sample and the bulk sample at the same viscosity is necessary.

Figure 18:
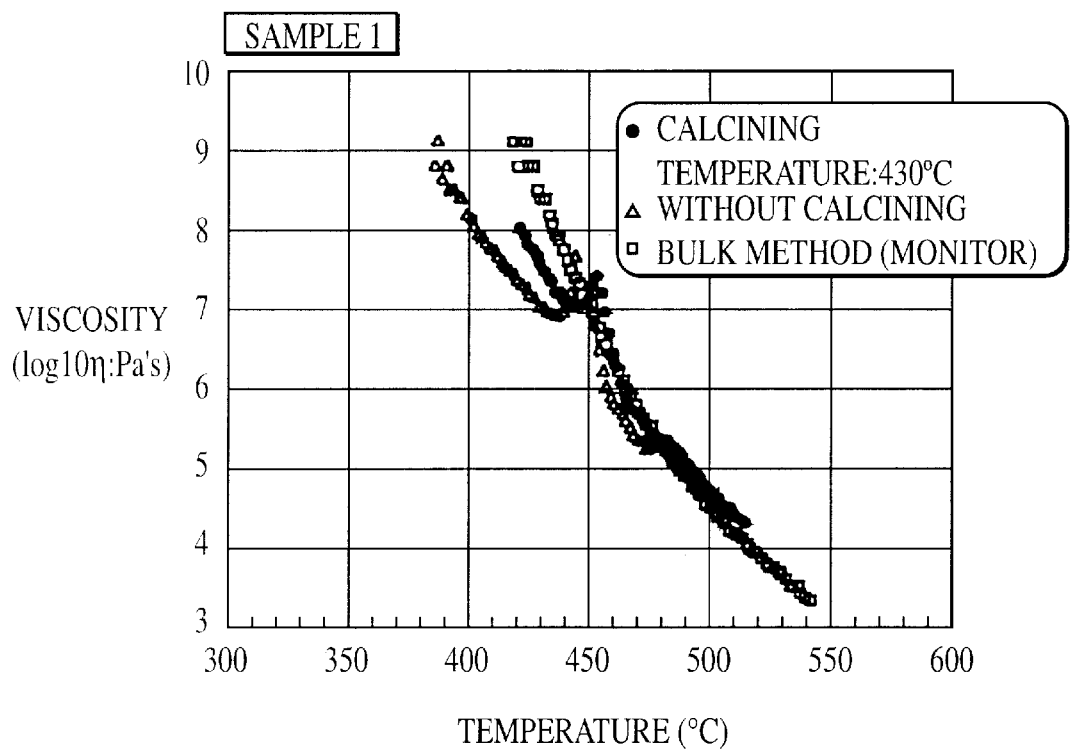
FIG. 18 is a graph showing a viscosity-temperature curve when a green compact sample of Sample 1 is calcined at the softening point minus 20° C. in the second embodiment of the present invention.
Figure 19:
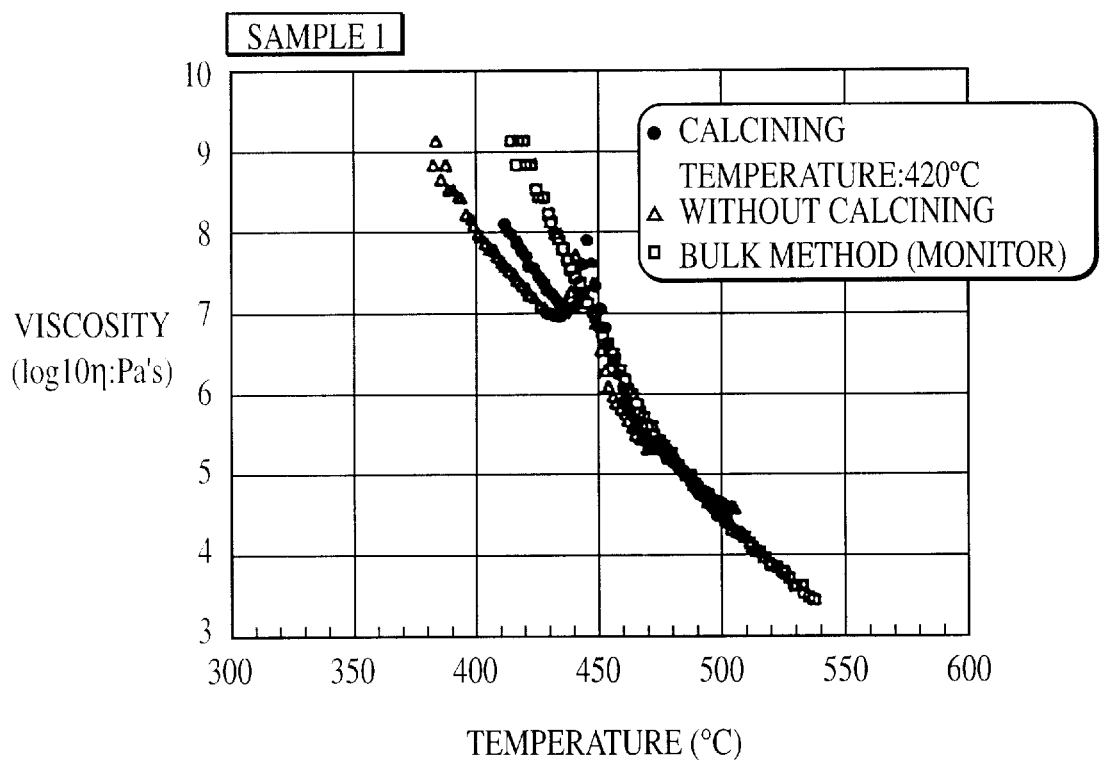
FIG. 19 is a graph showing a viscosity-temperature curve when a green compact sample of Sample 1 is calcined at the softening point minus 30° C. in the second embodiment of the present invention.
Figure 20:
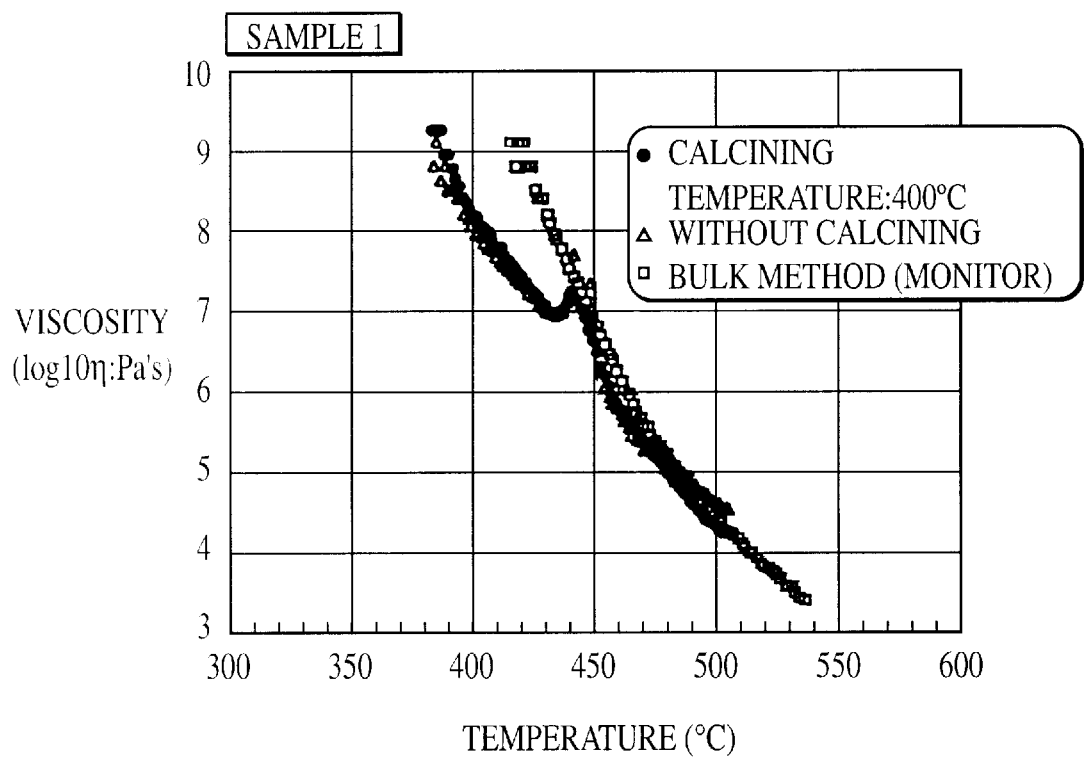
FIG. 20 is a graph showing a viscosity-temperature curve when a green compact sample of Sample 1 is calcined at the softening point minus 50° C. in the second embodiment of the present invention.

In contrast, when the green compact sample of Sample 1 was calcined at the softening point minus 20° C.(430° C.) under the condition (7), at the softening point minus 30° C. (420° C.) under the condition (8), and at the softening point minus 50° C. (400° C.) under the condition (9), as shown in FIGS. 18, 19, and 20, respectively, the viscosity-temperature curve indicated by ● for the calcined sample departed from the viscosity-temperature curve indicated by □ for the bulk sample and approached the viscosity-temperature curve indicated by Δ for the sample without calcining. The reason for this is believed to be that since the green compact sample was not sufficiently calcined at a temperature lower than the softening point minus 10° C., i.e., lower than 440° C., and powder particles were not sufficiently brought into close contact with each other.

Figure 21:
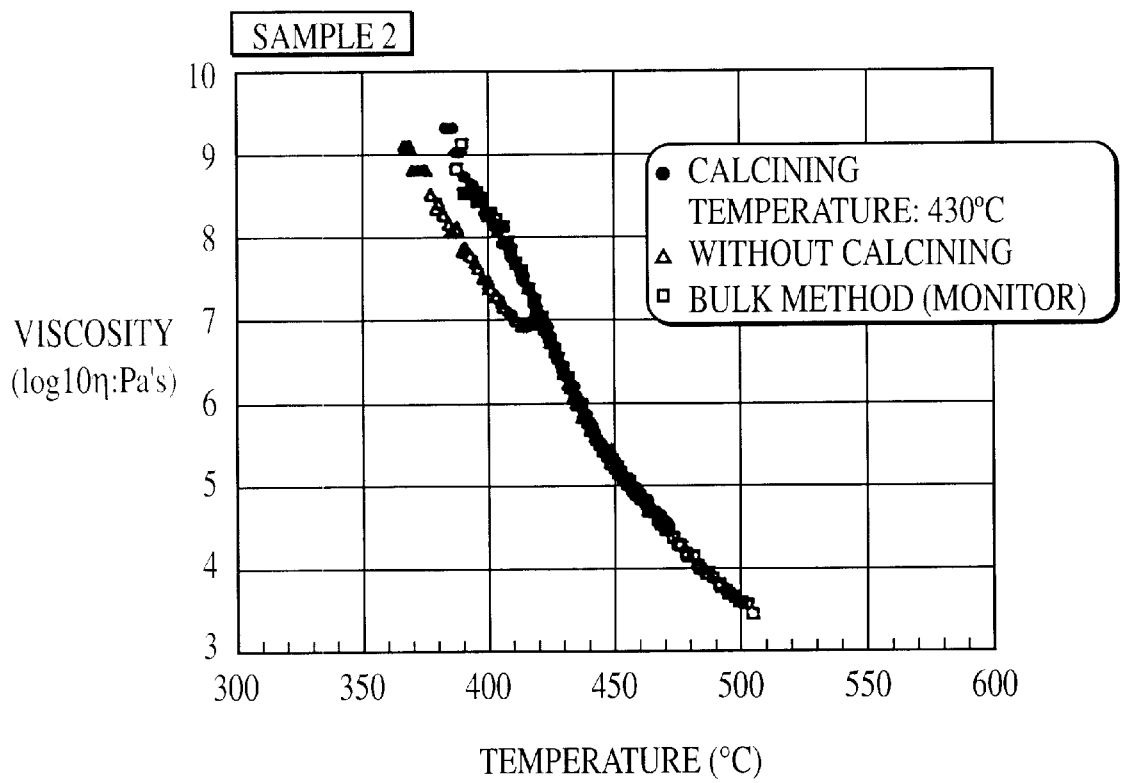
FIG. 21 is a graph showing a viscosity-temperature curve when a green compact sample of Sample 2 is calcined at the softening point in the second embodiment of the present invention.
Figure 22:
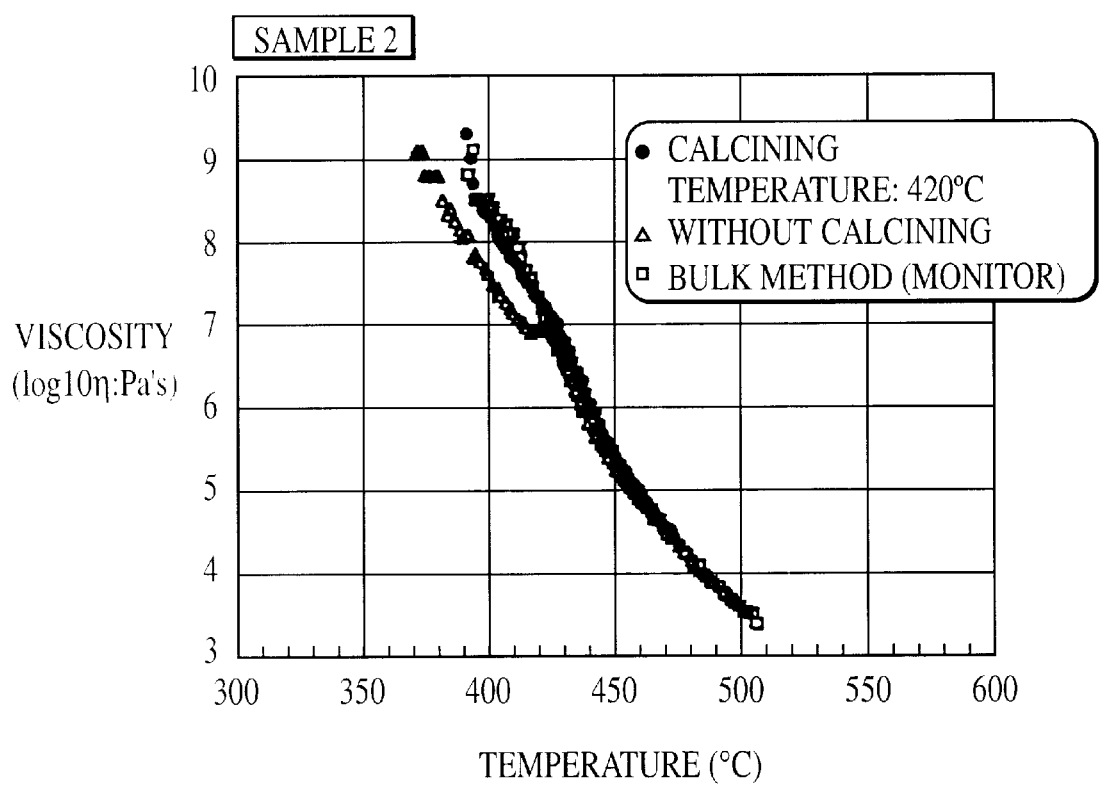
FIG. 22 is a graph showing a viscosity-temperature curve when a green compact sample of Sample 2 is calcined at the softening point minus 10° C. in the second embodiment of the present invention.

With respect to the green compact sample of Sample 2, when calcination was performed at the softening point, i.e., at 430° C., under the condition (5), as shown in FIG. 21, the viscosity-temperature curve indicated by ● for the calcined sample was close to the viscosity-temperature curve indicated by □ for the bulk sample. The reason for this is believed to be that since powder particles were sufficiently brought into close contact with each other in the green compact sample at the softening point, i.e., at 430° C., the viscous behavior thereof was very close to that of an incompressible fluid. When the calcination was performed at the softening point minus 10° C. (420° C.) under the conditions (6), as shown in FIG. 22, the viscosity-temperature curve indicated by ● for the calcined sample was also close to the viscosity-temperature curve indicated by □ for the bulk sample. The reason for this is believed to be that since powder particles were sufficiently brought into close contact with each other in the green compact sample even at the softening point minus 10° C., i.e., at 420° C., the viscous behavior thereof was very close to that of an incompressible fluid. Additionally, as a guideline for viscosity in this method, a difference in temperature of 2% or less between the calcined green compact sample and the bulk sample at the same viscosity is necessary.

Figure 23:
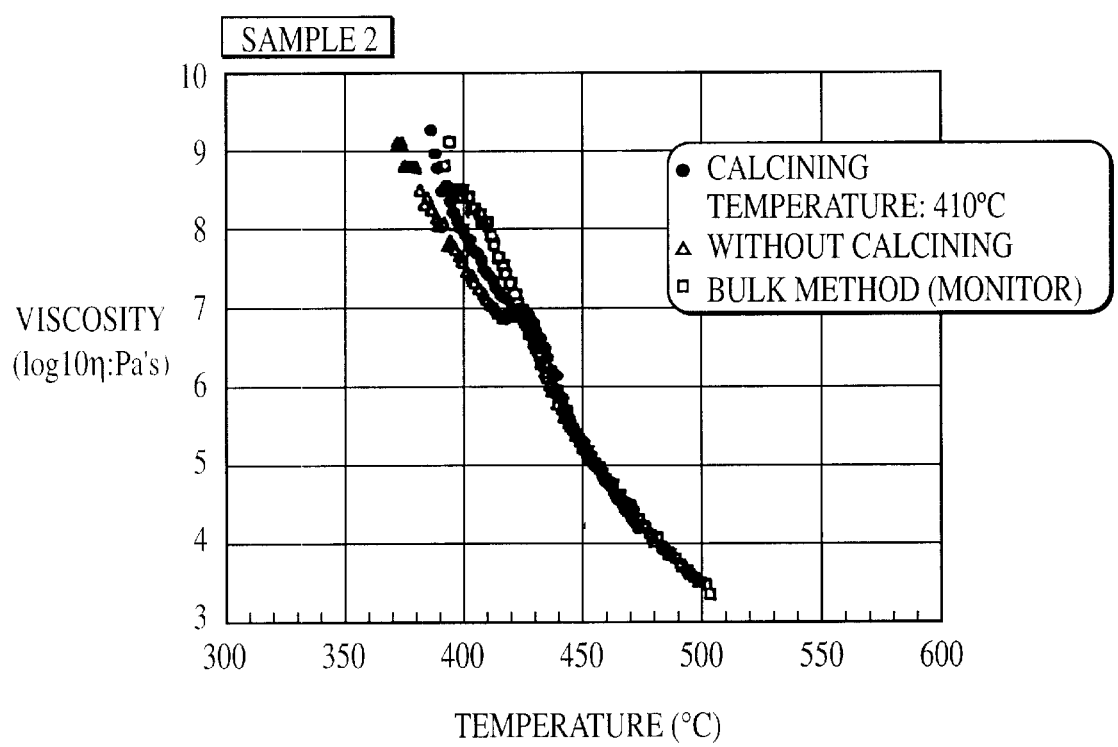
FIG. 23 is a graph showing a viscosity-temperature curve when a green compact sample of Sample 2 is calcined at the softening point minus 20° C. in the second embodiment of the present invention.
Figure 24:
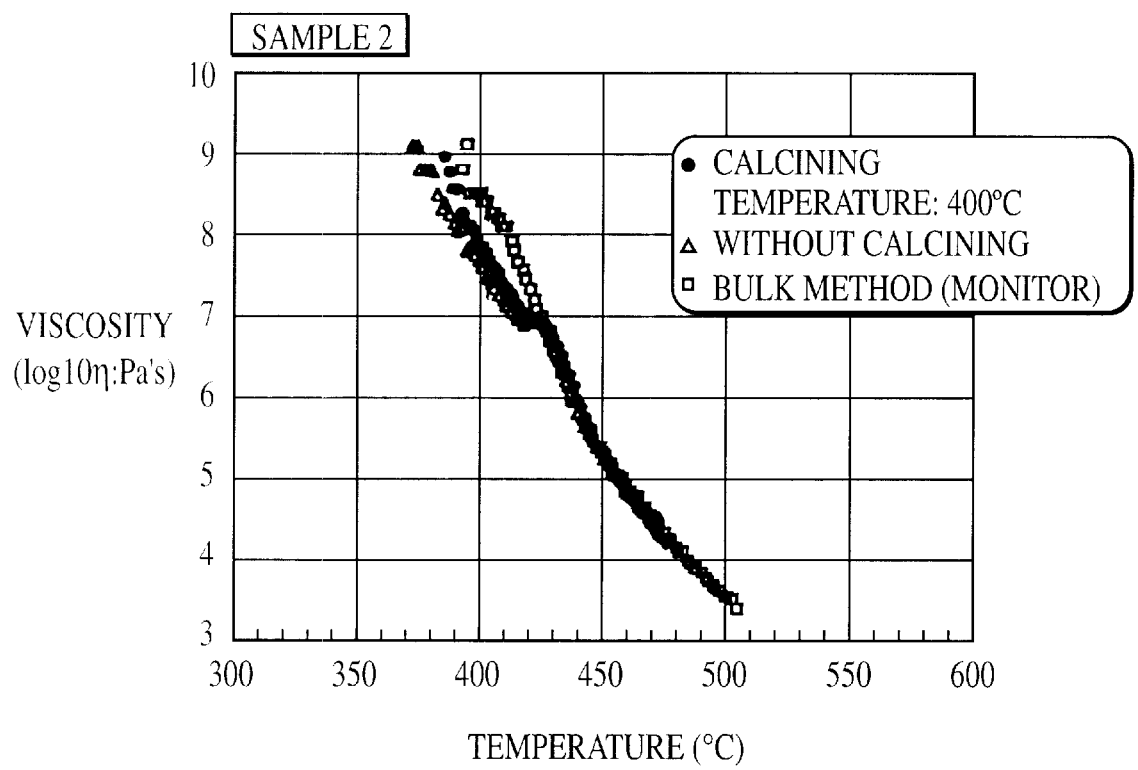
FIG. 24 is a graph showing a viscosity-temperature curve when a green compact sample of Sample 2 is calcined at the softening point minus 30° C. in the second embodiment of the present invention.
Figure 25:
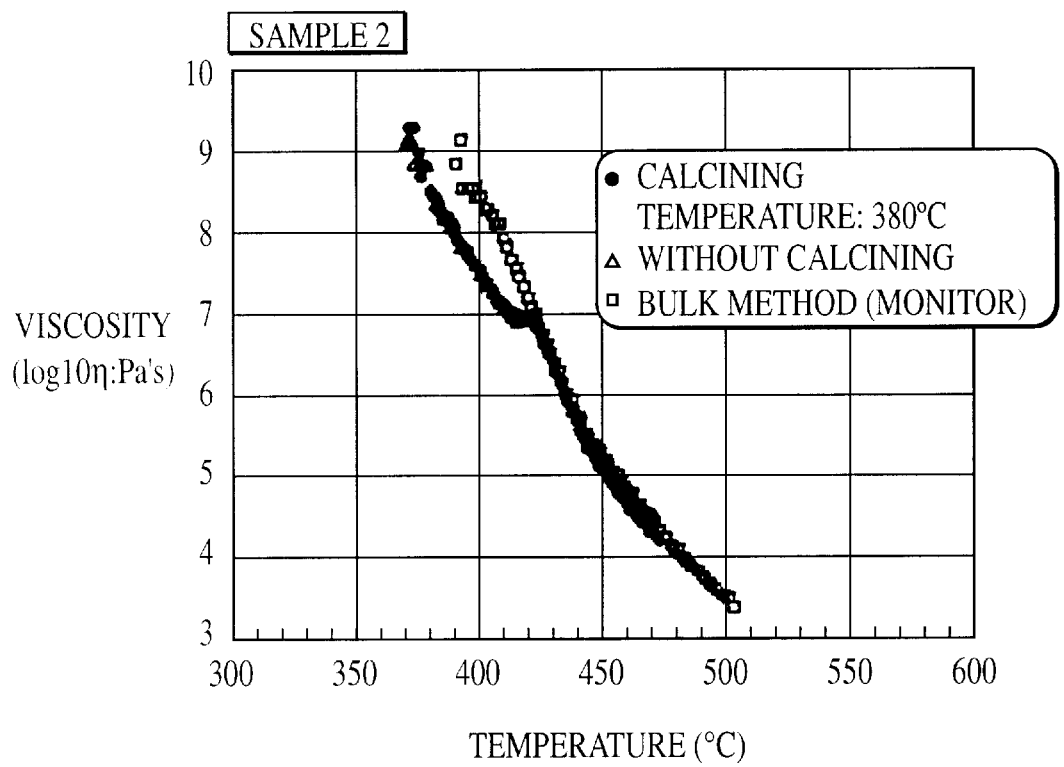
FIG. 25 is a graph showing a viscosity-temperature curve when a green compact sample of Sample 2 is calcined at the softening point minus 50° C. in the second embodiment of the present invention.

In contrast, when the green compact sample of Sample 2 was calcined at the softening point minus 20° C. (410° C.) under the condition (7), at the softening point minus 30° C. (400° C.) under the condition (8), and at the softening point minus 50° C. (380° C.) under the condition (9), as shown in FIGS. 23, 24, and 25, respectively, the viscosity-temperature curve indicated by ● for the calcined sample departed from the viscosity-temperature curve indicated by □ for the bulk sample and approached the viscosity-temperature curve indicated by A for the sample without calcining. The reason for this is believed to be that since the green compact sample was not sufficiently calcined at a temperature lower than the softening point minus 10° C., i.e., lower than 420° C., and powder particles were not sufficiently brought into close contact with each other.

Figure 26:
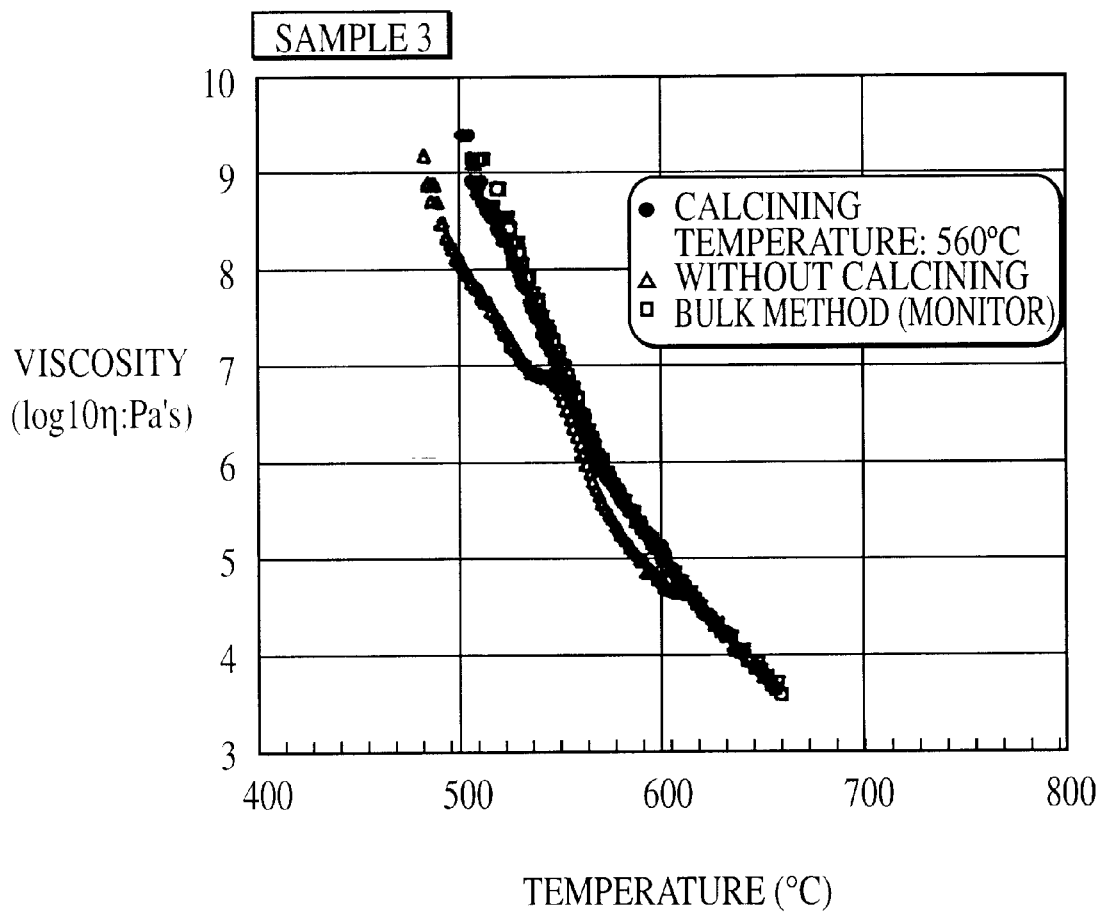
FIG. 26 is a graph showing a viscosity-temperature curve when a green compact sample of Sample 3 is calcined at the softening point in the second embodiment of the present invention.
Figure 27:
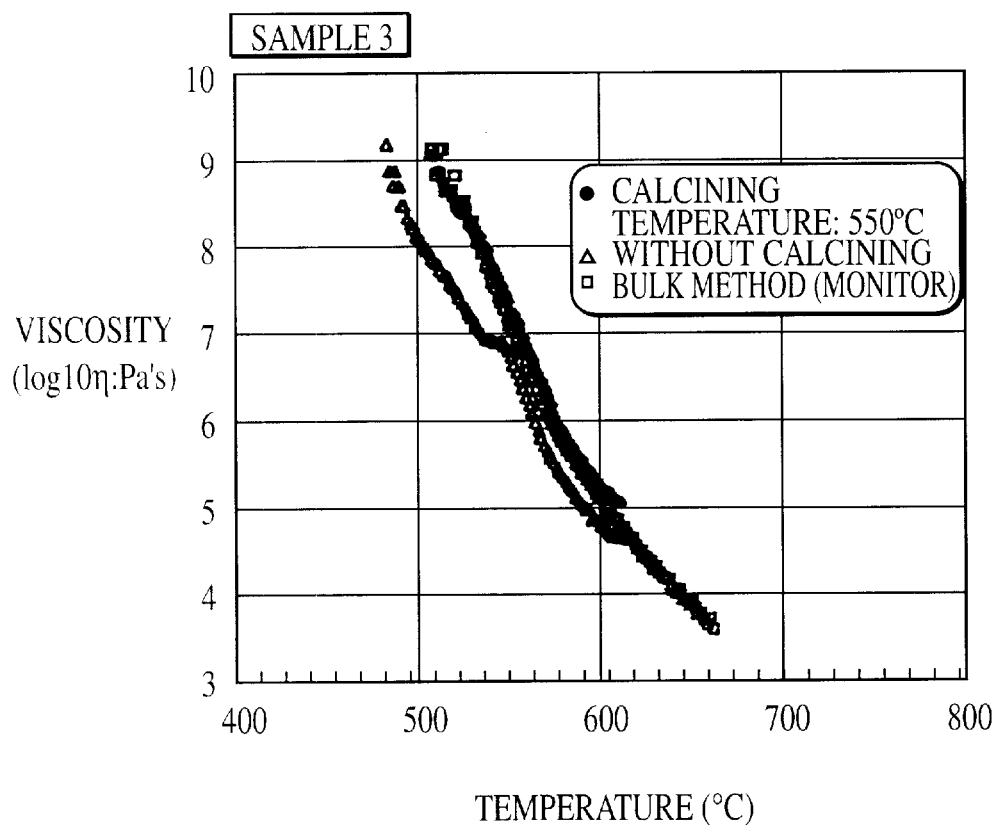
FIG. 27 is a graph showing a viscosity-temperature curve when a green compact sample of Sample 3 is calcined at the softening point minus 10° C. in the second embodiment of the present invention.
Figure 28:
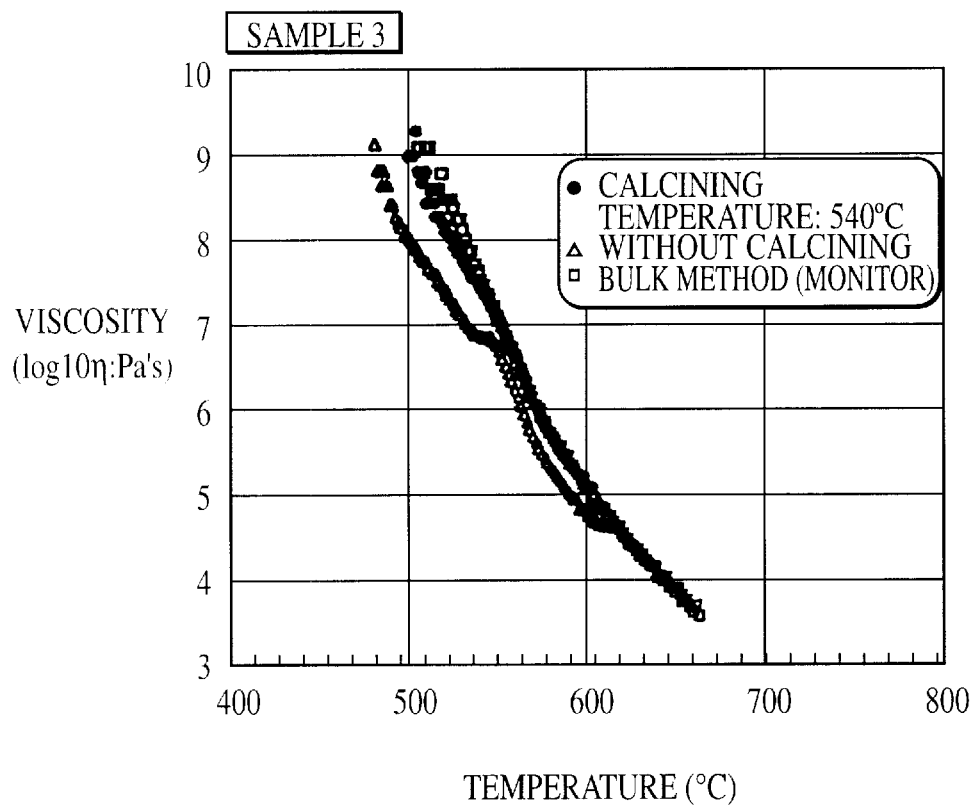
FIG. 28 is a graph showing a viscosity-temperature curve when a green compact sample of Sample 3 is calcined at the softening point minus 20° C. in the second embodiment of the present invention.
Figure 29:
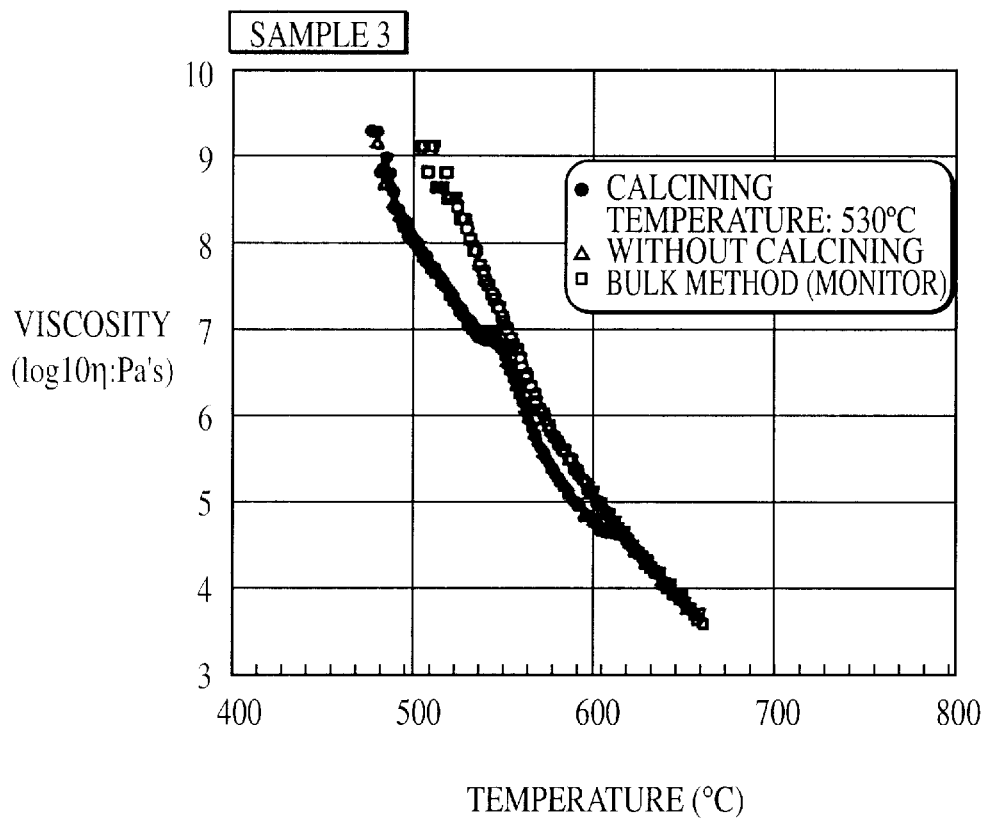
FIG. 29 is a graph showing a viscosity-temperature curve when a green compact sample of Sample 3 is calcined at the softening point minus 30° C. in the second embodiment of the present invention.

On the other hand, with respect to the green compact sample of Sample 3, when calcination was performed at the softening point, i.e., at 560° C., under the condition (5), as shown in FIG. 26, the viscosity-temperature curve indicated by ● for the calcined sample was close to the viscosity-temperature curve indicated by □ for the bulk sample. The reason for this is believed to be that since powder particles were sufficiently brought into close contact with each other in the green compact sample at the softening point, i.e., at 560° C., the viscous behavior thereof was very close to that of an incompressible fluid. When the calcination was performed at the softening point minus 10° C. (550° C.) under the condition (6), as shown in FIG. 27, the viscosity-temperature curve indicated by ● for the calcined sample was also close to the viscosity-temperature curve indicated by □ for the bulk sample. The reason for this is believed to be that since powder particles were sufficiently brought into close contact with each other in the green compact sample even at the softening point minus 10° C., i.e., at 550° C., the viscous behavior thereof was very close to that of an incompressible fluid. Furthermore, even when the calcination was performed at the softening point minus 20° C. (540° C.) under the condition (7) and at the softening point minus 30° C. (530° C.) under the condition (8), as shown in FIGS. 28 and 29, respectively, the viscosity-temperature curve indicated by ● for the calcined sample was also close to the viscosity-temperature curve indicated by □ for the bulk sample. The reason for this is believed to be that since powder particles were sufficiently brought into close contact with each other in the green compact sample even at the softening point minus 20° C., i.e., at 540° C. or at the softening point minus 30° C., i.e., at 530° C., the viscous behavior thereof was very close to that of an incompressible fluid. Additionally, as a guideline for viscosity in this method, a difference in temperature of 2% or less between the calcined green compact sample and the bulk sample at the same viscosity is necessary.

Figure 30:
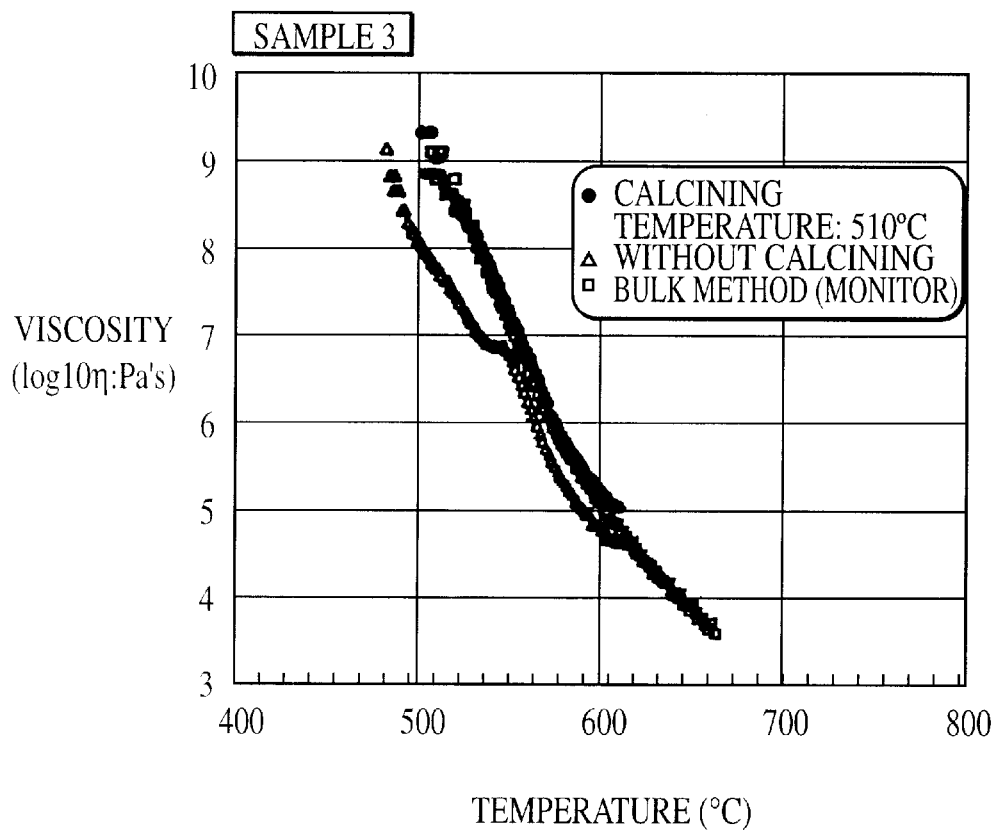
FIG. 30 is a graph showing a viscosity-temperature curve when a green compact sample of Sample 3 is calcined at the softening point minus 50° C. in the second embodiment of the present invention.

In contrast, when the green compact sample of Sample 3 was calcined at the softening point minus 50° C. (510° C.) under the condition (9), as shown in FIG. 30, the viscosity-temperature curve indicated by ● for the calcined sample departed from the viscosity-temperature curve indicated by □ for the bulk sample and approached the viscosity-temperature curve indicated by Δ for the sample without calcining. The reason for this is believed to be that since the green compact sample was not sufficiently calcined at a temperature lower than the softening point minus 30° C., i.e., lower than 530° C., and powder particles were not sufficiently brought into close contact with each other.

As is known from the above, the calcining temperature is preferably set at the softening point or less of the amorphous glass powder, and more preferably, is set in the range from the softening point minus 10° C. to the softening point, as generally applicable calcining conditions.

That is, by preliminarily calcining the green compact sample at an appropriate temperature, powder particles can be sufficiently brought into close contact with each other, and with respect to the green compact sample formed by compaction molding of inorganic powder, in particular, amorphous glass powder, the viscous behavior of the green compact sample can be evaluated and measured with high accuracy in the intermediate viscosity region of $10^4$ to $10^9$ Pa·s, which is particularly important in the sintering process, etc.

As described above, in accordance with the method for measuring the viscosity of the green compact sample, by preliminarily calcining the green compact sample formed by compaction molding of inorganic powder, such as amorphous glass powder, to sufficiently bring particles into close contact with each other, it is possible to measure the viscosity with high accuracy with respect to the green compact sample which exhibits viscous behavior that is very close to that of the inorganic powder in the powder state.

What is claimed is:

1. A method for measuring the viscosity η of a green compact sample formed by compaction molding of inorganic powder, the viscosity being measured in accordance with the Gent equation:

$$\eta = 2\pi MGH^5 / \{3V(dh/dt)(2\pi H^3 + V)\}$$

where M is the load, H is the height of the green compact sample, G is the gravitational acceleration, V is the volume of the green compact sample, and dh/dt is the deformation rate of the green compact sample, the method comprising the steps of:
(A) finding a corrected value V' of the sample volume of the green compact sample, where the corrected value V' of the sample volume is a volume occupied by the inorganic powder in the green compact sample;
(B) finding a corrected value (dh/dt)' of the sample deformation rate of the green compact sample, where the corrected value (dh/dt)' of the sample deformation rate is the difference between an apparent sample deformation rate and a sample deformation rate due to sintering shrinkage;
(C) separating a temperature range X in which sintering shrinkage dominates and a temperature range Y in which plastic deformation dominates with respect to the displacement of the green compact sample;
(D) substituting the corrected value V' of the sample volume for the sample volume V and substituting the corrected value (dh/dt)' of the sample deformation rate for the sample deformation rate dh/dt in the Gent equation with respect to the temperature range X in which sintering shrinkage dominates; and (E) substituting the corrected value V' of the sample volume for the sample volume V in the Gent equation with respect to the temperature range Y in which plastic deformation dominates.

2. A method for measuring the viscosity of a green compact sample according to claim 1, wherein:
a sample deformation rate $(dh/dt)_A$ at load A and a sample deformation rate $(dh/dt)_B$ at load B are obtained, each as the apparent sample deformation rate, where the load A is not equal to the load B;
by linear approximation using the sample deformation rate $(dh/dt)_A$ at load A and the sample deformation rate $(dh/dt)_B$ at load B, a sample deformation rate $(dh/dt)_0$ at zero load is obtained;
the sample deformation rate $(dh/dt)_0$ at zero load is considered as the sample deformation rate due to sintering shrinkage; and
a value obtained by subtracting the sample deformation rate $(dh/dt)_0$ at zero load from the sample deformation rate $(dh/dt)_A$ at load A or from the sample deformation rate $(dh/dt)_B$ at load B is set as the corrected value $(dh/dt)'$ of the sample deformation.

3. A method for measuring the viscosity of a green compact sample according to claim 2, wherein the load B is set greater than the load A, and the difference between the sample deformation rate $(dh/dt)_B$ at load B and the sample deformation rate $(dh/dt)_0$ at zero load is set as the corrected value $(dh/dt)'$ of the sample deformation rate.

4. A method for measuring the viscosity of a green compact sample according to one of claims 2 or 3, wherein a sample deformation rate versus temperature curve at zero load is plotted based on the sample deformation rate $(dh/dt)_0$ at zero load, the minimum value thereof is set as a boundary temperature $T_b$, the lower temperature side of the boundary temperature $T_b$ is set as the temperature range X in which sintering shrinkage dominates, and the higher temperature side of the boundary temperature $T_b$ is set as the temperature range Y in which plastic deformation dominates.

5. A method for measuring the viscosity of a green compact sample according to claim 4, wherein the apparent sample deformation rate is measured with a parallel plate viscometer.

6. A method for measuring the viscosity of a green compact sample according to claim 3, wherein the apparent sample deformation rate is measured with a parallel plate viscometer.

7. A method for measuring the viscosity of a green compact sample according to claim 2, wherein the apparent sample deformation rate is measured with a parallel plate viscometer.

8. A method for measuring the viscosity of a green compact sample according to claim 1, wherein the apparent sample deformation rate is measured with a parallel plate viscometer.

9. A method for measuring the viscosity of a green compact sample according to claim 1, wherein the inorganic powder is an inorganic oxide powder selected from the group consisting of crystallized glass powder, amorphous glass powder, and glass-ceramic composite powder.

10. An apparatus for measuring the viscosity $\eta$ of a green compact sample formed by compaction molding of inorganic powder, the viscosity being measured in accordance with the Gent equation:

$$\eta = 2\pi MGH^5/\{3V(dh/dt)(2\pi H^3 + V)\}$$

where M is the load, H is the height of the green compact sample, G is the gravitational acceleration, V is the volume of the green compact sample, and dh/dt is the deformation rate of the green compact sample,
the apparatus comprising:
a sample shape measuring unit (a) which measures actual shape values of the green compact sample;
a sample deformation rate measuring unit (b) which measures an apparent sample deformation rate of the green compact sample;
an arithmetic processing unit (c) which calculates the volume occupied by the inorganic powder in the green compact sample based on the actual shape values of the green compact sample and outputs a sample volume corrected value V';
an arithmetic processing unit (d) which calculates the difference between the apparent sample deformation rate and a sample deformation rate due to sintering shrinkage of the green compact sample and outputs a sample deformation rate corrected value $(dh/dt)'$ of the green compact sample;
an arithmetic processing unit (e) which plots a boundary temperature between a temperature range X in which sintering shrinkage dominates and a temperature range Y in which plastic deformation dominates with respect to a displacement of the green compact sample;
an arithmetic processing unit (f) which outputs the viscosity $\eta$ in the temperature range X by substituting the sample volume corrected value V' for the sample volume V and by substituting the sample deformation rate corrected value $(dh/dt)'$ for the sample deformation rate dh/dt in the Gent equation with respect to the temperature range X in which sintering shrinkage dominates;
an arithmetic processing unit (g) which outputs the viscosity $\eta$ in the temperature range Y by substituting the sample volume corrected value V' for the sample volume V in the Gent equation with respect to the temperature range Y in which plastic deformation dominates; and
a display (h) which displays the viscosity $\eta$ in the temperature range X and the viscosity $\eta$ in the temperature range Y.

11. An apparatus for measuring the viscosity of a green compact sample according to claim 10,
wherein the sample deformation rate measuring unit (b) outputs a sample deformation rate $(dh/dt)_A$ at load A and a sample deformation rate $(dh/dt)_B$ at load B, each as the apparent sample deformation rate, where the load A is not equal to the load B; and
the arithmetic processing unit (d) includes:
an arithmetic processing unit which outputs an extrapolated value at zero load, namely, a sample deformation rate $(dh/dt)_0$ at zero load, by linear approximation using the sample deformation rate $(dh/dt)_A$ at load A and the sample deformation rate $(dh/dt)_B$ at load B; and
an arithmetic processing unit which outputs a value obtained by subtracting the sample deformation rate $(dh/dt)_0$ at zero load from either the sample deformation rate $(dh/dt)_A$ at load A or the sample deformation rate $(dh/dt)_B$ at load B as the sample deformation rate corrected value $(dh/dt)'$, considering the sample deformation rate $(dh/dt)_0$ at zero load as the sample deformation rate due to sintering shrinkage.

12. An apparatus for measuring the viscosity of a green compact sample according to claim 11, wherein the load B is set greater than the load A, and the arithmetic processing unit (d) outputs the difference between the sample deformation rate $(dh/dt)_B$ at load B and the sample deformation rate $(dh/dt)_0$ at zero load as the sample deformation rate corrected value $(dh/dt)'$.

13. An apparatus for measuring the viscosity of a green compact sample according to one of claims 11 or 12, wherein the arithmetic processing unit (e) plots a sample deformation rate versus temperature curve at zero load based on the sample deformation rate $(dh/dt)_0$ at zero load, sets the minimum value thereof as a boundary temperature $T_b$, and extracts the lower temperature side of the boundary temperature $T_b$ as the temperature range X in which sintering shrinkage dominates and the higher temperature side of the boundary temperature $T_b$ as the temperature range Y in which plastic deformation dominates.

14. An apparatus for measuring the viscosity of a green compact sample according to claim 13, wherein the sample deformation rate measuring unit (b) which measures the apparent sample deformation rate comprises a parallel plate viscometer.

15. An apparatus for measuring the viscosity of a green compact sample according to claim 12, wherein the sample deformation rate measuring unit (b) which measures the apparent sample deformation rate comprises a parallel plate viscometer.

16. An apparatus for measuring the viscosity of a green compact sample according to claim 11, wherein the sample deformation rate measuring unit (b) which measures the apparent sample deformation rate comprises a parallel plate viscometer.

17. An apparatus for measuring the viscosity of a green compact sample according to claim 10, wherein the sample deformation rate measuring unit (b) which measures the apparent sample deformation rate comprises a parallel plate viscometer.

18. An apparatus for measuring the viscosity of a green compact sample according to claim 13, wherein said arithmetic processing units are comprised in a computer.

19. An apparatus for measuring the viscosity of a green compact sample according to claim 12, wherein said arithmetic processing units are comprised in a computer.

20. An apparatus for measuring the viscosity of a green compact sample according to claim 11, wherein said arithmetic processing units are comprised in a computer.

21. An apparatus for measuring the viscosity of a green compact sample according to claim 10, wherein said arithmetic processing units are comprised in a computer.

22. A computer readable recording medium storing a program for executing a method for measuring the viscosity of a green compact sample according to claim 4.

23. A computer readable recording medium storing a program for executing a method for measuring the viscosity of a green compact sample according to claim 3.

24. A computer readable recording medium storing a program for executing a method for measuring the viscosity of a green compact sample according to claim 2.

25. A computer readable recording medium storing a program for executing a method for measuring the viscosity of a green compact sample according to claim 1.

* * * * *